United States Patent
DeGregorio

(10) Patent No.: US 10,154,970 B2
(45) Date of Patent: Dec. 18, 2018

(54) METHODS FOR IMMUNOMODULATION OF CANCER AND INFECTIOUS DISEASE THERAPY

(71) Applicant: The Regents of the University of California, Oakland, CA (US)

(72) Inventor: Michael W. DeGregorio, Granite Bay, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/623,585

(22) Filed: Jun. 15, 2017

(65) Prior Publication Data

US 2018/0000747 A1  Jan. 4, 2018

Related U.S. Application Data

(63) Continuation of application No. PCT/US2015/066805, filed on Dec. 18, 2015.

(60) Provisional application No. 62/096,487, filed on Dec. 23, 2014.

(51) Int. Cl.

| | | |
|---|---|---|
| A61K 31/035 | (2006.01) | |
| A61K 31/085 | (2006.01) | |
| A61K 39/00 | (2006.01) | |
| A61K 39/12 | (2006.01) | |
| A61K 39/39 | (2006.01) | |
| A61K 45/06 | (2006.01) | |
| A61K 31/055 | (2006.01) | |
| A61K 31/09 | (2006.01) | |
| A61K 31/137 | (2006.01) | |
| A61K 31/138 | (2006.01) | |
| A61K 31/192 | (2006.01) | |
| A61K 31/216 | (2006.01) | |
| A61K 31/353 | (2006.01) | |
| A61K 31/5377 | (2006.01) | |
| A61K 31/5415 | (2006.01) | |
| A61K 33/24 | (2006.01) | |

(52) U.S. Cl.
CPC .......... *A61K 31/035* (2013.01); *A61K 31/055* (2013.01); *A61K 31/085* (2013.01); *A61K 31/09* (2013.01); *A61K 31/137* (2013.01); *A61K 31/138* (2013.01); *A61K 31/192* (2013.01); *A61K 31/216* (2013.01); *A61K 31/353* (2013.01); *A61K 31/5377* (2013.01); *A61K 31/5415* (2013.01); *A61K 33/24* (2013.01); *A61K 39/0011* (2013.01); *A61K 39/12* (2013.01); *A61K 39/39* (2013.01); *A61K 45/06* (2013.01); *A61K 2039/545* (2013.01); *A61K 2039/55* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 4,990,538 | A | 2/1991 | Harris et al. |
| 5,788,964 | A | 8/1998 | Baral et al. |
| 5,859,065 | A | 1/1999 | Brandes |
| 6,528,681 | B2 | 3/2003 | Kaltenbach, III et al. |
| 7,452,901 | B2 * | 11/2008 | Boojamra ............ A61K 31/675 514/300 |
| 2006/0079478 | A1 | 4/2006 | Boojamra et al. |
| 2011/0312925 | A1 | 12/2011 | Labrie |
| 2012/0263677 | A1 | 10/2012 | Eagle et al. |
| 2014/0363500 | A1 | 12/2014 | Dumontet et al. |

FOREIGN PATENT DOCUMENTS

| | | |
|---|---|---|
| WO | 98/58634 A2 | 12/1998 |
| WO | 2001/36360 | 5/2001 |
| WO | 2016/106146 | 6/2016 |

OTHER PUBLICATIONS

Degregorio et al., "L-BLP25 vaccine plus letrozole for breast cancer," OncoImmunology 2012, 1:8, pp. 1422-1424.
Kao et al., "Assessing the Effects of Concurrent versus Sequential Cisplatin/Radiotherapy on Immune Status in Lung Tumor—Bearing C57BL/6 Mice," Cancer Immunol Res, Jul. 2015, 3(7), pp. 741-750.
Karpuzoglu-Sahin et al., "Interferon-levels are upregulated by 17-β-estradiol and Diethylstilbestrol," Journal of Reproductive Immunology, 2001, vol. 52, pp. 113-127.
Suzuki et al., "Salutary effects of 17β-estradiol on T-cell signaling and cytokine production after trauma-hemorrhage are mediated primarily via estrogen receptor-α," Am J Physiol Cell Physiol, Jun. 2007, vol. 292, pp. C2103-C2111.
Wurz et al., "Antitumor effects of L-BLP25 Antigen-Specific tumor immunotherapy in a novel human MUC1 transgenic lung cancer mouse model," Journal of Translational Medicine, 2013, 11:64, 13 pages.

* cited by examiner

*Primary Examiner* — Heidi Reese
(74) *Attorney, Agent, or Firm* — Kilpatrick Townsend & Stockton LLP

(57) ABSTRACT

The present invention provides methods for modulating the immune response of a subject to a therapeutic agent, the method comprising administering an effective amount of a triphenylethylene (TRIP) compound with an effective amount of the therapeutic agent. In particular embodiments, the TRIP compound enhances the immune response of the subject to the therapeutic agent. In some embodiments, the TRIP compound is administered in different dosing schedules to provide a biphasic immunomodulation effect.

33 Claims, 19 Drawing Sheets

| | Scramble | BP25 | Range | >300 SFC | >1000 SFC |
|---|---|---|---|---|---|
| Control | | | 13-218 | 0/5 | 0/5 |
| TRIP 100 mg/kg | | | 7-183 | 0/6 | 0/6 |
| PV 100 µg | | | 326-1360 | 6/6 | 1/6 |
| TRIP + PV | | | 302-6295 | 6/6 | 4/6 |

FIG. 19

METHODS FOR IMMUNOMODULATION OF CANCER AND INFECTIOUS DISEASE THERAPY

CROSS-REFERENCES TO RELATED APPLICATIONS

This application is a continuation of International Patent Application No. PCT/US2015/066805, filed Dec. 18, 2015, which claims priority to U.S. Provisional Patent Application No. 62/096,487, filed Dec. 23, 2014, which applications are incorporated herein by reference in their entirety for all purposes.

BACKGROUND OF THE INVENTION

Human cancers frequently express tumor associated antigens (TAAs) that are altered forms of self-proteins or epitopes with very limited or no expression on normal cells. Over the past few decades, the list of known TAAs has greatly increased (Vigneron N. et al., *Cancer Immun* 13:15 (2013)). Interestingly, because the immune surveillance system is continuously exposed to self-antigens, T cells that recognize high-affinity, major histocompatibility complex (MHC)-associated immunodominant epitopes get deleted through a thymic selection process. On the other hand, T cells that recognize low-affinity subdominant epitopes of TAAs are left behind during the selection process. These T cells, which recognize subdominant epitopes of self-proteins, can be recruited by vaccination for the induction of an immune response (Cibotti R. et al., *Proc Natl Acad Sci USA*, 416-20 (1992)). Simply described, these TAAs are recognized by the host immune system as foreign, resulting in an antitumor immune response.

Over the years, identification of several TAAs has spurred the development of cancer vaccines and active specific immunotherapies for cancer designed to boost an immune response. Cancer vaccines offer a new therapeutic direction by inducing an immune response that can persist long after the vaccine therapy has been discontinued. In contrast, chemotherapy and small, targeted molecules directly affect tumor cells only during the period of administration. Furthermore, cancer vaccines can theoretically induce a more robust immune response with minimal toxicity.

In recent years, multiple studies have demonstrated that cellular [T helper type 1 ($T_H1$) and cytotoxic T lymphocyte (CTL)-mediated] rather than humoral [T helper type 2 ($T_H2$) antibody-mediated] immune responses are responsible for the rejection of transplanted tumors or allogeneic tissues in experimental animal models (Kirkwood J M. et al., *CA Cancer J Clin.*, 62:309-35 (2012); Melero I. et al., *Nat Rev Clin Oncol.* 11:509-24 (2014); Rosenberg S A., *Nature.*, 411:380-4 (2001)). A $T_H1$-polarized immune response involving CTLs and natural killer (NK) cells mediates the elimination of tumor cells, while a $T_H2$-polarized immune response can have deleterious effects by promoting tumor development and progression (Kirkwood J M. et al., *CA Cancer J Clin.*, 62:309-35 (2012); Curigliano G. et al., *Breast.*, 22 Suppl 2:S96-9 (2013)). Therefore, significant efforts have been directed toward the identification of TAAs recognized by human T lymphocytes to mount a cellular immune response (Boon T. et al., *Immunol Today.*, 18:267-8 (1997); Rosenberg S A., *Immunity*, 10:281-7 (1999)). This is not to say that antibody-based anticancer immunotherapies are ineffective against solid tumors. Indeed, the past decade has seen the clinical development of numerous monoclonal antibodies directed at growth factors such as vascular endothelial growth factor (VEGF), growth factor receptors such as human epidermal growth factor receptor (EGFR) and negative immune checkpoint regulators such as cytotoxic T lymphocyte-associated antigen 4 (CTLA-4) and programmed cell death receptor 1 (PD-1) (Sliwkowski M X. et al., *Science.*, 341:1192-8 (2013)).

Although chemotherapy has been traditionally believed to antagonize immunotherapy, it is now becoming apparent that conventional chemotherapy has significant "off-target" immunological effects (Kandalaft L E. et al., *Gynecol Oncol.*, 116:222-33 (2010)). Earlier studies have clearly highlighted the role of the immune system in cancer clearance. In mouse models of solid tumors, increased inflammation following chemotherapy predicts better prognosis (Kepp 0. et al., *Apoptosis*, 14:364-75 (2009)), while tumors in immunodeficient mice do not respond to the chemotherapy (Obeid M. et al., *Cancer Res.*, 67:7941-4 (2007)). Similarly, the presence of tumor-infiltrating lymphocytes (TIL) in breast cancer patients following neo-adjuvant chemotherapy predicted complete pathological response (Hornychova H. et al., *Cancer Invest.* 26:1024-31 (2008)).

Tumor inflammation has been shown to be involved in many stages of tumor development and progression (Grivennikov S I. et al., *Cell*, 140:883-99 (2010)). The influence of inflammation on the immune system's response to tumors, in conjunction with its known tumorigenic properties, can potentially be utilized in cancer immunotherapy (Dougan M. et al., *Annu Rev Immunol.*, 27:83-117 (2009)) and enhance the response to chemotherapy (Zhu Z. et al., *Mediators Inflamm.*, 2012:528690 (2012); Zitvogel L. et al., *Nat Rev Immunol.*, 8:59-73 (2008)). However, the antitumor effects of cancer chemotherapy can also be weakened by inflammation (Ammirante M. et al., *Nature*, 464:302-5 (2010)). Thus, cancer-related inflammation remains a target for novel therapeutic strategies.

To summarize, the identification of TAAs in various cancers has made the development of cancer immunotherapies an attractive area of pharmaceutical research. The efficacy of chemotherapy is known to be affected by inflammation, which is also a target for novel therapeutic strategies. Agents that can regulate the inflammatory microenvironment created by tumorigenesis and chemotherapy may improve the response to both antigen-specific cancer immunotherapies and chemoradiotherapy through immunomodulation.

With respect to infectious disease, intense efforts are currently underway to develop effective vaccines and other immunotherapies to combat viral infections such as Ebola virus. According to the latest data from the World Health Organization, the current (2014-15) epidemic of Ebola virus disease, formerly known as Ebola hemorrhagic fever, in western Africa had claimed more than 11,000 lives as of early November 2015. Several different strategies, including monoclonal antibodies (Qiu X. et al., *Nature*, 514:47-53 (2014)), RNA interference (Geisbert T W. et al., *Lancet.*, 375:1896-905 (2010)), and a bivalent vaccine based on the rabies virus vaccine (Blaney J E. et al., *PLoS Pathog.*, 9:e1003389 (2013)), have been studied, and several Phase I clinical trials are already underway or are planned in the near future. The symptoms associated with a fatal outcome in an Ebola virus infection are a poorly regulated inflammatory immune response coupled with immune suppression. Accordingly, agents that can regulate the inflammatory response of the immune system may improve the response to the therapeutic agents through immunomodulation. Identification of such agents could improve the survival rate of Ebola virus infections and similar diseases.

Additionally, it is known that the immune response in people aged 50 and older, and especially in those aged 65 and over, is generally weaker compared to younger subjects due to the phenomenon known as immunosenescence (Goronzy J. et al., *Nat. Immunol.*, 14:428-36 (2013)). This results in a reduced ability to mount an effective immune response against infection as well as the vaccines used to prevent such infections. Thus, the identification of agents that can augment the immune response in older or immunocompromised individuals suffering from various viral, bacterial, or other infectious diseases is desirable.

As such, there is a need in the art for agents that can modulate an immune response to a therapeutic agent in a subject. The present invention addresses this need and provides related advantages as well.

BRIEF SUMMARY OF THE INVENTION

In some aspects, the present invention provides a method for modulating an immune response to a therapeutic agent in a subject, the method including administering an effective amount of a TRIP compound or a pharmaceutically acceptable salt thereof in combination with an effective amount of the therapeutic agent to the subject.

In particular aspects, the present invention provides a method for modulating an immune response to a therapeutic agent in a subject, the method including administering an effective amount of a compound according to Formula I:

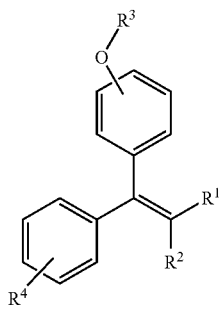

(I)

or a pharmaceutically acceptable salt thereof in combination with an effective amount of the therapeutic agent to the subject;

wherein:

$R^1$ and $R^2$ are selected from the group consisting of

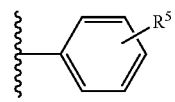

and a $C_{1-8}$ haloalkyl, wherein when $R^1$ is

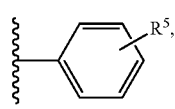

$R^2$ is a $C_{1-8}$ haloalkyl, and when $R^1$ is a $C_{1-8}$ haloalkyl, $R^2$ is

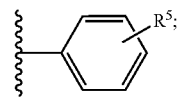

the $C_{1-8}$ haloalkyl comprises a halogen X; and
$R^3$, $R^4$, and $R^5$ are independently selected from the group consisting of hydrogen, a hydroxyl, a $C_{1-18}$ alkylhydroxy, and an alkoxy.

In some embodiments, the compound of Formula I is represented by Formula Ia or Ib:

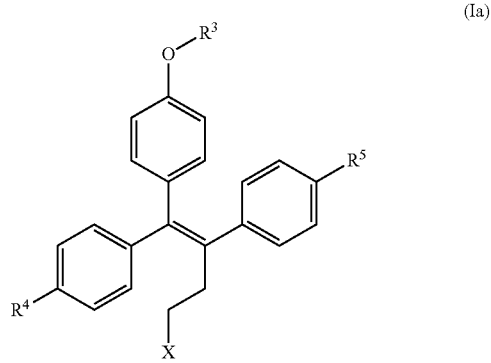

(Ia)

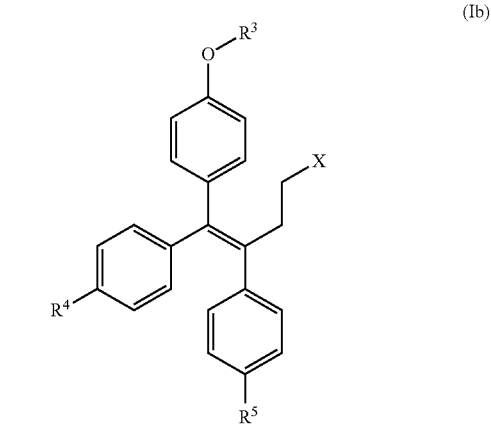

(Ib)

wherein, $R^3$ is an alkoxy or alkylhydroxyl, $R^4$ is hydrogen or a hydroxyl, $R^5$ is hydrogen, and X is Cl.

In some embodiments, the subject has or is at risk of developing cancer.

In particular embodiments, the therapeutic agent for a subject having or at risk of developing cancer is selected from the group consisting of a chemotherapeutic agent, a radiotherapeutic agent, an antigen-specific immunotherapeutic agent, an endocrine therapy, a tyrosine kinase inhibitor, a thalidomide derivative, and combinations thereof. In some instances, the antigen-specific immunotherapeutic agent is selected from the group consisting of a vaccine, an antibody, cytotoxic T lymphocytes (CTLs), chimeric antigen receptor T cells (CAR-T cells), and combinations thereof. In some instances, the vaccine is a peptide vaccine.

In some embodiments, subject has or is at risk of developing an infectious disease. In some instances, the infectious disease is caused by a virus, a bacterium, a fungi, or a parasite.

In particular embodiments, the therapeutic agent for a subject having or at risk of developing an infectious disease is selected from the group consisting of an antigen-specific immunotherapeutic agent, an antiviral, an antibiotic, an antifungal, a thalidomide derivative, and combinations thereof. In some instances, the antigen-specific immunotherapeutic agent is a vaccine or an antibody. In some instances, the vaccine is a peptide vaccine.

In some embodiments, the TRIP compound (e.g., compound of Formula I) enhances the immune response of the subject to the therapeutic agent. In some instances, the TRIP compound (e.g., compound of Formula I) enhances the immune response by improving the T cell response, augmenting the innate T cell immune response, decreasing inflammation, inhibiting T regulatory cell activity, or combinations thereof.

In some embodiments, the TRIP compound (e.g., compound of Formula I) is administered before the therapeutic agent is administered. In some embodiments, the TRIP compound (e.g., compound of Formula I) is administered at the same time as the therapeutic agent.

In some embodiments, the effective amount of the TRIP compound (e.g., compound of Formula I) is an amount sufficient to first improve the T cell response and then decrease inflammation.

In some embodiments, different doses of the TRIP compound (e.g., compound of Formula I) are administered to the subject in accordance with a sequential dosing regimen.

In some embodiments, sequential dosing of a TRIP compound (e.g., compound of Formula I) includes administering a first dosing regimen of an effective amount of the TRIP compound (e.g., compound of Formula I) in combination with an effective amount of a first therapeutic agent to the subject, wherein the effective amount of the TRIP compound (e.g., compound of Formula I) is an amount sufficient to enhance the T cell response to the first therapeutic agent, and administering a second dosing regimen of an effective amount of the TRIP compound (e.g., compound of Formula I) in combination with an effective amount of a second therapeutic agent to the subject, wherein the effective amount of the TRIP compound (e.g., compound of Formula I) is an amount sufficient to decrease inflammation and enhance the response to the second therapeutic agent.

In some embodiments, the first therapeutic agent is an antigen-specific immunotherapeutic agent. In some instances, the antigen-specific immunotherapeutic agent is selected from the group consisting of a vaccine, an antibody, cytotoxic T lymphocytes (CTLs), chimeric antigen receptor T cells (CAR-T cells), and combinations thereof.

In some embodiments, the second therapeutic agent is selected from the group consisting of a chemotherapeutic agent, a radiotherapeutic agent, an endocrine therapy, a tyrosine kinase inhibitor, an antiviral, an antibiotic, an antifungal, a thalidomide derivative, and combinations thereof.

In some embodiments, the first dosing regimen comprises a high dose of the TRIP compound (e.g., compound of Formula I), and the second dosing regimen comprises a low dose of the TRIP compound (e.g., compound of Formula I).

In another aspect, the present invention provides a kit including one or more TRIP compounds (e.g., one or more compounds of Formula I), and one or more therapeutic agents.

In some embodiments the kit also includes a label with instructions for administering the one or more TRIP compounds (e.g., one or more compounds of Formula I) and/or the one or more therapeutic agents.

In some embodiments, the one or more therapeutic agents are selected from the group consisting of an antigen-specific immunotherapeutic agent, a chemotherapeutic agent, a radiotherapeutic agent, an endocrine therapy, a tyrosine kinase inhibitor, an antiviral, an antibiotic, an antifungal, a thalidomide derivative, and combinations thereof. In some instances, the antigen-specific immunotherapeutic agent is selected from the group consisting of a vaccine, an antibody, cytotoxic T lymphocytes (CTLs), chimeric antigen receptor T cells (CAR-T cells), and combinations thereof.

Other objects, features, and advantages of the present invention will be apparent to one of skill in the art from the following detailed description and figures.

BRIEF DESCRIPTION OF THE DRAWINGS

FIG. 19. IFN-γ immune response to scrambled and BP25 peptides following treatment with control (n=5), TRIP 100 mg/kg (n=6), PV 100 μg (n=6) and the TRIP+PV (n=6) combination. Each of four weekly 100 μg injections of peptide vaccine (PV) was preceded by three daily oral doses of TRIP. All mice were implanted with breast cancer allografts on Day 0, and spleens were collected for enzyme-linked immunosorbent spot (ELISpot) analysis on Day 28 following four weeks of treatment. The BP25 peptide is a 25-mer and the target antigen of the PV, while the scrambled peptide is a control peptide containing the same 25 amino acids in a scrambled arrangement. Representative ELISpot results are displayed for the scrambled and BP25 peptides for each treatment group along with the range of spot forming cells (SFC)/5.0×10$^5$ total cells and the number of subjects with more than 300 and 1000 SFCs, respectively, in response to the BP25 peptide.

DETAILED DESCRIPTION OF THE INVENTION

I. Introduction

Figure 1:
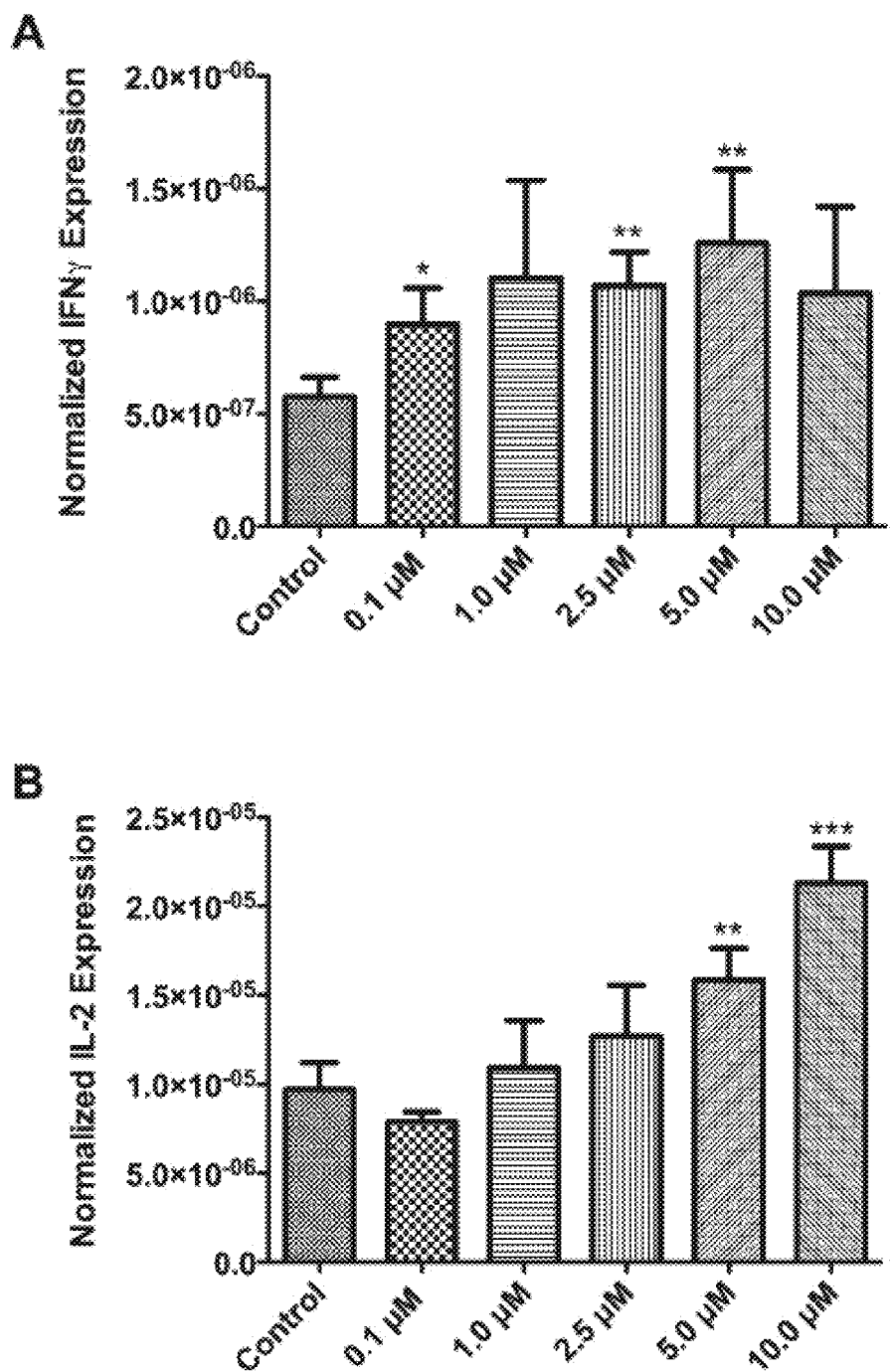
FIG. 1. Interferon gamma (IFN-γ) and interleukin (IL)-2 expression in human Jurkat cells following exposure to TRIP in vitro. Jurkat cells ($2 \times 10^6$) were treated with different concentrations of TRIP as indicated for 24 hours. (A) IFN-γ and (B) IL-2 mRNA expression levels were detected by quantitative real-time polymerase chain reaction (qRT-PCR) and normalized with the expression of GAPDH. *$p<0.05$, $p<0.01$, *$p<0.001$.

The present disclosure relates, in part, to the use of the triphenylethylenes (TRIPs) and chemical derivatives, isomers, or metabolites thereof to modulate the immune system for the purpose of enhancing the immune response to immunotherapies such as cancer vaccines as well as vaccines against infectious diseases. For example, TRIPs can be administered in combination with a cancer vaccine to boost the innate and adaptive immune response of a subject to the cancer vaccine, potentially improving the subject's prognosis. TRIPs can also be useful in treating cancer and infectious disease when administered in combination with one or more drugs with no known immunologic effects. For example, TRIPs can be administered with an antimicrobial agent to boost the innate and adaptive immune response of a subject to an infection, while the antimicrobial agent is administered to act directly on the infection. The boosted immune response induced by TRIP administration could potentially result in the subject overcoming the infection faster than using the antimicrobial agent alone.

In certain aspects, TRIPs also possess a biphasic action, in that the immune response elicited in a subject can be dependent on the dosing amount administered. A high dosing regimen of TRIPs can induce one immunologic effect, while a low dosing regimen can induce a second effect. For example, a first dosing regimen can enhance T cell response, and a second dosing regimen can reduce inflammation. Utilizing the biphasic action of these modulators, it is possible to enhance antigen-specific immune responses and reduce the inflammatory responses to both cancer and infectious diseases.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "subject", "patient" or "individual" are used herein interchangeably to include a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

As used herein, the term "administering" includes oral administration, topical contact, administration as a suppository, intravenous, intraperitoneal, intramuscular, intralesional, intrathecal, intranasal, or subcutaneous administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering an effective amount of the compounds described herein for enhancing an immune response in an individual to a therapeutic agent, for example by improving the T cell response, augmenting the innate T cell immune response, decreasing inflammation, inhibiting T regulatory cell activity or combinations thereof.

The term "effective amount" or "therapeutically effective amount" includes an amount or quantity effective, at dosages and for periods of time necessary, to produce a desired (e.g., therapeutic or prophylactic) result with respect to the indicated disease, disorder, or condition. The desired result may comprise a subjective or objective improvement in the recipient of the effective amount. In one non-limiting example, an effective amount of one or more TRIPs includes an amount or dosage sufficient to improve T cell response to a therapeutic agent. Also, for example, an effective amount includes an amount or dosage sufficient to decrease inflammation. The effective amount will vary with the type of subject being treated and the compound or combination of compounds applied.

The term "vaccine" includes a composition administered to a subject to enhance an immune response. The enhanced immune response may include improving the T cell response, supplementing the innate T cell immune response, reducing or decreasing inflammation, inhibiting T regulatory cell activity, increasing antibody response, and combinations thereof. The composition of the vaccine may include any causative agent of a disease, its products, or a synthetic substitute including, but not limited to, peptides, peptide fragments, and fusion proteins.

The term "enhance the immune response" includes modulating the immune system of an individual having cancer or an infectious disease. Modulating includes increasing T cell response, augmenting innate T cell immune response, decreasing inflammation, inhibiting T regulatory cell activity, increasing antibody response, and combinations thereof. In some instances, an enhanced immune response is lowering the inflammation so that a therapeutic agent may be more efficacious. In some instances, an enhanced immune response is an increase in T cell response targeting cancerous or infected cells.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of $—(CH_2)_n—$, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

"Haloalkyl" refers to alkyl, as defined above, where one of the hydrogen atoms is replaced with a halogen atom. The halogen atom may be F, Cl, I, or Br, and may be located at any position in the alkyl chain, including the terminal carbon. As for the alkyl group, haloalkyl groups can have any suitable number of carbon atoms, such as $C_{1-8}$ (i.e., $C_1$, $C_2$, $C_3$, $C_4$, $C_5$, $C_6$, $C_7$, $C_8$). Other chain lengths include $C_{1-2}$, $C_{1-3}$, $C_{1-4}$, $C_{1-5}$, $C_{1-6}$, $C_{1-7}$ or longer.

"Halogen" or "halo" refers to fluorine, chlorine, bromine and iodine.

"Alkylhydroxy" refers to an alkyl group, as defined above, where at least one of the hydrogen atoms is replaced with a hydroxy group. In preferred embodiments, alkylhydroxy refers to an alkyl group, as defined above, where a hydrogen of the terminal carbon atom is replaced with a hydroxyl group. As for the alkyl group, alkylhydroxy groups can have any suitable number of carbon atoms, such as $C_{1-6}$. Other carbon lengths include, but are not limited to $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, up to $C_{1-18}$. Exemplary alkylhydroxy groups include, but are not limited to, hydroxy-methyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like.

"Alkoxy" refers to an alkyl group having at least one bridging oxygen atom. The bridging oxygen atom can be anywhere within the alkyl chain (alkyl-O-alkyl) or the bridging oxygen atom can connect the alkyl group to the point of attachment (alkyl-O—). Alkyl components linking bridging oxygen atoms (—O-alkyl-O—) are at least divalent, an alkylene. In instances where the point of attachment for the alkoxy group is a heteroatom, the linking atom of the alkoxy is a carbon. In some instances, the alkoxy contains 1, 2, 3, 4, 5 or more bridging oxygen atoms. As for the alkyl group, alkoxy groups can have any suitable number of total carbon atoms, such as $C_{1-4}$, $C_{1-5}$, $C_{1-6}$, $C_{1-7}$, and $C_{1-8}$. Alkoxy groups can be substituted or unsubstituted. In preferred embodiments, the terminal carbon of the alkoxy chain is substituted with a hydroxyl. Exemplary alkoxy groups with terminal hydroxyls include:

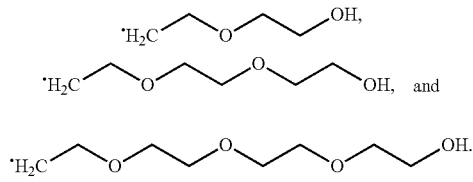

The terms "compound of Formula I," "triphenylethylene," "TRIP," and "TRIP compound" are used interchangeably to refer to the compounds described herein that modulate the immune system to enhance an immune response in an individual.

III. Description of the Embodiments

The present invention provides methods for modulating an immune response of a subject to a therapeutic agent, the method comprising administering an effective amount of a triphenylethylene (TRIP) compound with an effective amount of the therapeutic agent. In particular embodiments, the TRIP compound enhances the immune response of the subject to the therapeutic agent. In some embodiments, the TRIP compound is administered in different dosing schedules to provide a biphasic immunomodulation effect. The present invention further provides kits comprising a TRIP compound with one or more therapeutic agents.

A. TRIP Compounds

Triphenylethylenes (TRIPs) are triphenyl derivatives of ethylene. The compounds of the present invention include three phenyl groups attached and one aliphatic hydrocarbon as substituents of the central ethylene group. In some embodiments, the aliphatic hydrocarbon group comprises a halogen substituent. In particular embodiments, the halogen substituent is at the terminal carbon.

In certain aspects, the triphenylethylene (TRIP) compounds described herein are compounds according to Formula I:

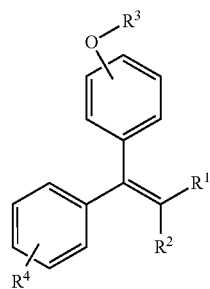

or a pharmaceutically acceptable salt wherein
$R^1$ and $R^2$ are selected from the group consisting of

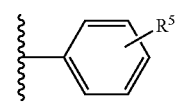

and a $C_{1-8}$ haloalkyl, wherein when $R^1$ is

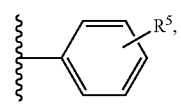

$R^2$ is a $C_{1-8}$ haloalkyl, and when $R^1$ is a $C_{1-8}$ haloalkyl, $R^2$ is

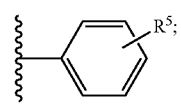

the $C_{1-8}$ haloalkyl comprises a halogen X; and
$R^3$, $R^4$, and $R^5$ are independently selected from the group consisting of hydrogen, a hydroxyl, a $C_{1-18}$ alkylhydroxy, and an alkoxy.

In some embodiments, the aliphatic $C_{1-8}$ haloalkyl group is a $C_{1-4}$ haloalkyl group. In some embodiments, the aliphatic $C_{1-8}$ haloalkyl group is

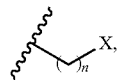

wherein
the subscript n is an integer selected from the group consisting of 1, 2, 3, and 4.

In some embodiments, the $C_{1-4}$ haloalkyl group is a $C_2$ alkyl group with a terminal halogen substitution, shown below where the halogen is represented as an X:

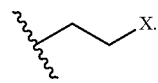

In some embodiments, the halogen substitution X is Cl.

In some embodiments, $R^3$, $R^4$, $R^5$ are independently selected from the group consisting of hydrogen, a hydroxyl, a $C_{2-10}$ alkylhydroxy, and an alkoxy, wherein the alkoxy comprises $C_{2-6}$ and at least one bridging oxygen atom.

In some embodiments $R^1$ is a

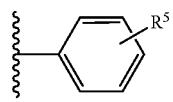

and $R^2$ is a $C_{1-4}$ haloalkyl, and $R^3$, $R^4$, and $R^5$ are independently selected from the group consisting of hydrogen, a hydroxyl, a $C_{2-10}$ alkylhydroxy, and an alkoxy, wherein the alkoxy comprises $C_{2-6}$ and at least one bridging oxygen atom.

In some embodiments $R^1$ is a $C_{1-4}$ haloalkyl and $R^2$ is a

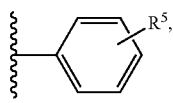

and $R^3$, $R^4$, and $R^5$ are independently selected from the group consisting of hydrogen, a hydroxyl, a $C_{2-10}$ alkylhydroxy, and an alkoxy, wherein the alkoxy comprises $C_{2-6}$ and at least one bridging oxygen atom.

In some embodiments, $R^1$ is

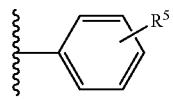

and $R^2$ is

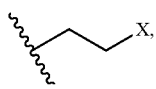

and $R^3$, $R^4$, and $R^5$ are independently selected from the group consisting of hydrogen, a hydroxyl, a $C_{2-10}$ alkylhydroxy, and an alkoxy, wherein the alkoxy comprises $C_{2-6}$ and at least one bridging oxygen atom and X is a halogen atom. In some embodiments, X is Cl.

In some embodiments, $R^1$ is

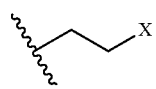

and $R^2$ is a

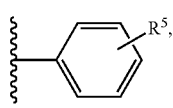

and $R^3$, $R^4$, and $R^5$ are independently selected from the group consisting of hydrogen, a hydroxyl, a $C_{2-10}$ alkylhydroxy, and an alkoxy, wherein the alkoxy comprises $C_{2-6}$ and at least one bridging oxygen atom and X is a halogen atom. In some embodiments, X is Cl.

In some embodiments, the compound of Formula I is represented by Formula Ia or Ib:

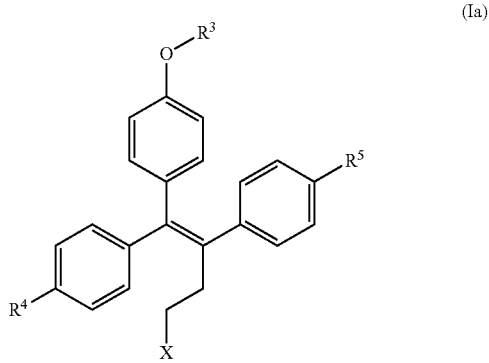

(Ia)

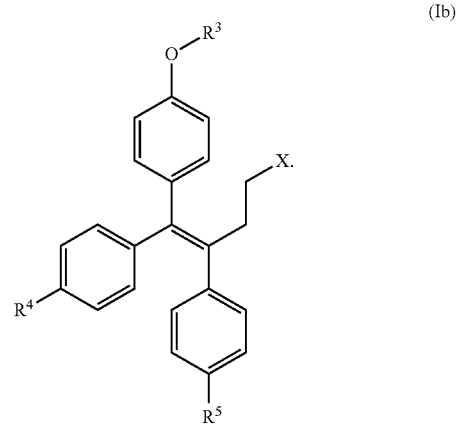

(Ib)

In some embodiments, $R^3$ is an alkoxy or alkylhydroxyl, $R^4$ is hydrogen or a hydroxyl, $R^5$ is hydrogen or a hydroxyl, and X is a halogen. In some embodiments, X is Cl.

In some embodiments, $R^3$ is

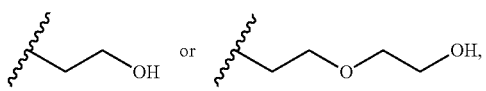

$R^4$ is hydrogen or a hydroxyl, $R^5$ is hydrogen or a hydroxyl, and X is a halogen. In some embodiments, X is Cl.

In certain embodiments, the compound of Formula Ia is ospemifene, wherein $R^3$ is

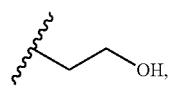 [SMILES: *CCO]

$R^4$ is hydrogen, $R^5$ is hydrogen, and X is Cl.

In certain other embodiments, the compound of Formula Ia is fispemifene, wherein $R^3$ is

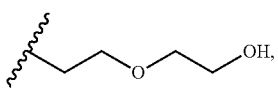 [SMILES: *CCOCCO]

$R^4$ is hydrogen, $R^5$ is hydrogen, and X is Cl.

The TRIP compounds (e.g., compounds of Formula I) can be prepared by methods commonly employed in the art. As non-limiting examples, ospemifene and fispemifene can be synthesized as described in Examples 1 and 2, respectively.

Metabolites of the compounds disclosed herein are also with the scope of the present invention. For example, known metabolites of ospemifene include a hydroxyl group at one or both positions $R^4$ and $R^5$.

B. Therapeutic Agents

The TRIP compounds of the present invention can be used in combination with a therapeutic agent to enhance the immune response of a subject receiving treatment. The therapeutic agent used will depend on the disease or condition afflicting the subject (e.g., cancer or an infection).

Non-limiting examples of therapeutic agents include chemotherapeutic agents, radiotherapeutic agents, antigen-specific immunotherapeutic agents, endocrine therapies, tyrosine kinase inhibitors, antiviral agents, antibiotics, antifungal agents, thalidomide derivatives, and combinations thereof.

In some embodiments, the therapeutic agents of the present invention are agents that themselves possess immunologic effects. When administered in combination with TRIP compounds, the immunologic effects of the therapeutic agents are enhanced. In other embodiments, the therapeutic agents of the present invention are agents that are not known to possess immunologic effects. When administered in combination with TRIP compounds, a subject's immune response is boosted to better combat the disease or condition afflicting the subject (e.g., cancer or an infection), and the immunomodulatory (e.g., anti-inflammatory) activity of the TRIP compounds complements the effects of the (non-immunomodulating) therapeutic agent. As a non-limiting example, a subject having a bacterial infection can be administered a TRIP compound in combination with an antibiotic that acts directly on the infection to the point where the subject's immune system is able to take over and eradicate the infection, and the TRIP compound boosts or augments the subject's innate and adaptive immune responses to eradicate the infection. As another non-limiting example, a subject having pneumonitis caused by a viral infection can be administered a TRIP compound in combination with an antiviral agent that acts directly on the virus itself, while the TRIP compound acts via its immunomodulatory (e.g., anti-inflammatory) activity to decrease the inflammation of lung tissue associated with pneumonitis.

1. Chemotherapeutic Agents

Chemotherapeutic agents (e.g., anti-cancer agents) are well known in the art and include, but are not limited to, anthracenediones (anthraquinones) such as anthracyclines (e.g., daunorubicin (daunomycin; rubidomycin), doxorubicin, epirubicin, idarubicin, and valrubicin), mitoxantrone, and pixantrone; platinum-based agents (e.g., cisplatin, carboplatin, oxaliplatin, satraplatin, picoplatin, nedaplatin, triplatin, and lipoplatin); tamoxifen and metabolites thereof such as 4-hydroxytamoxifen (afimoxifene) and N-desmethyl-4-hydroxytamoxifen (endoxifen); taxanes such as paclitaxel (taxol) and docetaxel; alkylating agents (e.g., nitrogen mustards such as mechlorethamine (HN2), cyclophosphamide, ifosfamide, melphalan (L-sarcolysin), and chlorambucil); ethylenimines and methylmelamines (e.g., hexamethylmelamine, thiotepa, alkyl sulphonates such as busulfan, nitrosoureas such as carmustine (BCNU), lomustine (CCNLJ), semustine (methyl-CCN—U), and streptozoein (streptozotocin), and triazenes such as decarbazine (DTIC; dimethyltriazenoimidazolecarboxamide)); antimetabolites (e.g., folic acid analogues such as methotrexate (amethopterin), pyrimidine analogues such as fluorouracil (5-fluorouracil; 5-FU), floxuridine (fluorodeoxyuridine; FUdR), and cytarabine (cytosine arabinoside), and purine analogues and related inhibitors such as mercaptopurine (6-mercaptopurine; 6-MP), thioguanine (6-thioguanine; 6-TG), and pentostatin (2'-deoxycofonnycin)); natural products (e.g., vinca alkaloids such as vinblastine (VLB) and vincristine, epipodophyllotoxins such as etoposide and teniposide, and antibiotics such as dactinomycin (actinomycin D), bleomycin, plicamycin (mithramycin), and mitomycin (mitomycin Q); enzymes such as L-asparaginase; biological response modifiers such as interferon alpha); substituted ureas such as hydroxyurea; methyl hydrazine derivatives such as procarbazine (N-methylhydrazine; MIH); adrenocortical suppressants such as mitotane (o,p'-DDD) and aminoglutethimide; analogs thereof derivatives thereof and combinations thereof.

In particular embodiments, the TRIP compounds described herein are useful when administered in combination with chemotherapeutic agents such as anthracyclines (e.g., daunorubicin, doxorubicin, epirubicin, idarubicin, valrubicin, and/or mitoxantrone) and/or platinum-based agents (e.g., cisplatin, carboplatin, oxaliplatin, satraplatin, picoplatin, nedaplatin, triplatin, and/or lipoplatin).

2. Radiotherapeutic Agents

Radiotherapeutic agents are well known in the art and can comprise external-beam radiation therapy and/or internal radiation therapy. External beam radiation therapy delivers radioactive beams of high energy X-rays and/or gamma rays to a patient's tumor, whereas internal radiation therapy delivers radioactive atoms to a patient's tumor. Both external beam radiation therapy and internal radiation therapy are used to suppress tumor growth or kill cancer cells by delivering a sufficient quantity of radioactivity to the target site. In some embodiments, the radiotherapeutic agent comprises a radioactive atom and is complexed with a biologic or synthetic agent to increase delivery to the target site. Such biologic or synthetic agents are known in the art. Suitable radioactive atoms for use with the TRIP compounds of the present invention include any of the radionuclides described herein, or any other isotope which emits enough energy to destroy a targeted tissue or cell. In some embodiments, radiotherapeutic agents may be coupled to targeting moieties, such as antibodies, to improve the localization of radiotherapeutic agents to cancerous or infected cells.

The term "radionuclide" is intended to include any nuclide that exhibits radioactivity. A "nuclide" refers to a type of atom specified by its atomic number, atomic mass, and energy state, such as carbon 14 ($^{14}$C). "Radioactivity" refers to the radiation, including alpha particles, beta particles, nucleons, electrons, positrons, neutrinos, and gamma rays, emitted by a radioactive substance. Examples of radionuclides suitable for use in the present invention include, but are not limited to, fluorine 18 ($^{18}$F), fluorine 19 ($^{19}$F), phosphorus 32 ($^{32}$P), scandium 47 ($^{47}$Sc), cobalt 55 ($^{55}$Co), copper 60 ($^{60}$Cu), copper 61 ($^{61}$Cu), copper 62 ($^{62}$Cu), copper 64 ($^{64}$Cu), gallium 66 ($^{66}$Ga) copper 67 ($^{67}$Cu), gallium 67 ($^{67}$Ga), gallium 68 ($^{68}$Ga), rubidium 82 ($^{82}$Rb), yttrium 86 ($^{86}$Y), yttrium 87 ($^{87}$Y), strontium 89 ($^{89}$Sr), yttrium 90 ($^{90}$Y), rhodium 105 ($^{105}$Rh) silver 111 ($^{111}$Ag)

indium 111 ($^{111}$In), iodine 124 ($^{124}$I), iodine 125 ($^{125}$I), iodine 131 ($^{131}$I), tin 117m ($^{117m}$Sn), technetium 99m ($^{99m}$Tc), promethium 149 ($^{149}$Pm), samarium 153 ($^{153}$Sm), holmium 166 ($^{166}$Ho), lutetium 177 ($^{177}$Lu), rhenium 186 ($^{186}$Re) rhenium 188 ($^{188}$Re) thallium 201 ($^{201}$Tl), astatine 211 ($^{211}$At), and bismuth 212 ($^{212}$Bi). As used herein, the "m" in $^{117m}$Sn and $^{99m}$Tc stands for the meta state. Additionally, naturally-occurring radioactive elements such as uranium, radium, and thorium, which typically represent mixtures of radioisotopes, are suitable examples of radionuclides. $^{67}$Cu, $^{131}$I, $^{177}$Lu, and $^{186}$Re are beta- and gamma-emitting radionuclides. $^{212}$Bi is an alpha- and beta-emitting radionuclide. $^{211}$At is an alpha-emitting radionuclide. $^{32}$P, $^{47}$Sc, $^{89}$Sr, $^{90}$Y $^{105}$Rh, $^{111}$Ag, $^{117m}$Sn, $^{149}$Pm, $^{153}$Sm, $^{166}$Ho, and $^{188}$Re are examples of beta-emitting radionuclides. $^{67}$Ga, $^{111}$In, $^{99m}$Tc, and $^{201}$Tl are examples of gamma-emitting radionuclides. $^{55}$Co, $^{60}$Cu, $^{61}$Cu, $^{62}$Cu, $^{66}$Ga, $^{68}$Ga, $^{82}$Rb, and $^{86}$Y are examples of positron-emitting radionuclides. $^{64}$Cu is a beta- and positron-emitting radionuclide.

3. Antigen-Specific Immunotherapeutic Agents

In some embodiments, antigen-specific immunotherapeutic agents include compounds and compositions designed to stimulate the immune system to specifically recognize antigens expressed or overexpressed by infected or cancerous cells. In other embodiments, antigen-specific immunotherapeutic agents include compounds and compositions that will specifically recognize antigens expressed or overexpressed by infected or cancerous cells. Non-limiting examples of antigen-specific immunotherapeutic agents include vaccines (e.g., peptide vaccines), antibodies, cytotoxic T cell lymphocytes (CTLs), chimeric antigen receptor T cells (CAR-T cells), and combinations thereof. In particular embodiments, the antigens presented by infected or cancerous cells are highly specific to each disease or condition, and the vaccines, antibodies, CTLs, and/or CAR-T cells used is dependent on the disease or condition being treated.

A vaccine can stimulate the immune system to specifically recognize and attack antigens presented by infected or cancerous cells. Vaccines can comprise one or more peptides, peptide fragments, fusion peptides, DNA, RNA, inactivated infectious agent virus, bacterium, fungi, parasite, or other infectious agent), attenuated (weakened) infectious agent, other biologic or non-biologic material, or combinations thereof.

In some embodiments, at least 1, 2, 3, 4, 5, 6, 7, 8, 9, 10, 11, 12, 13, 14, 15 or more peptides, peptide fragments, or fusion peptides may be used for a peptide vaccine. The peptides may be harvested from an endogenous source or chemically synthesized. The peptides chosen are specific for the infection or type of cancer being treated. For example, when targeting a viral infection the peptide, peptide fragments, or fusion peptides chosen will be those of the virus of interest that are likely to be presented by the infected cells. A person of skill in the art will be aware of the most promising peptides to use based on the disease or condition being treated. When targeting cancer cells, some commonly targeted proteins include GM-CSF, IL-13Rα2, EphA2, and Survivin; however, specific cancer types will have specifically preferred peptides used for targeting afflicted cells. In some embodiments, the one or more peptides in the peptide vaccine are free soluble peptides. In other embodiments, the one or more peptides in the peptide vaccine are tethered together using any means known in the art.

In some embodiments, vaccines include pneumococcal vaccines such as, e.g., PCV13 vaccine, PPSV23 vaccine, PCV7 vaccine, and combinations thereof. In some embodiments, vaccines include cancer vaccines such as, e.g., tecemotide (L-BLP25), oncophage, sipuleucel-T, and combinations thereof. Tecemotide (L-BLP25) is a liposomal antigen-specific cancer immunotherapy that contains 25 amino acids from the immunogenic tandem-repeat region of MUC1 (see, e.g., Mehta N R et al., *Clin. Cancer Res.*, 18:2861-2871 (2012)). In some embodiments, vaccines include Ebola vaccines such as, e.g., VSV-EBOV vaccine.

Antibodies can recognize antigens expressed or overexpressed by infected or cancerous cells. Antigens recognized by these antibodies can be proteins expressed, activated, or overexpressed on the cell surface or proteins secreted into the extracellular fluid. In some embodiments, antibodies can be used to target human effector cells (e.g., macrophages) against the infected or cancerous cells. In some embodiments, antibodies are used to inhibit the normal function of cell surface receptors. In some embodiments, antibodies bind to the ligands of cell surface receptors to block the cellular signaling cascade. Antibodies used as antigen-specific immunotherapeutic agents can be monoclonal or polyclonal antibodies as well as chimeric, humanized, or human antibodies, and can be previously isolated from the patient or produced from another biologic source. Methods of producing antibodies are well known in the art, and may be made by any known means. For example, antibodies described herein can be produced by conventional monoclonal antibody methodology e.g., the standard somatic cell hybridization technique of Kohler and Milstein, *Nature* 256: 495 (1975), the contents of which are herein incorporated by reference for all purposes. In some embodiments, antibodies useful in the treatment of cancer include immune checkpoint inhibitors. In particular embodiments, antibodies useful in the treatment of cancer include, but are not limited to, alemtuzumab, bevacizumab, cetuximab, ipilimumab, nivolumab, ofatumumab, panitumumab, pembrolizumab, atezolizumab, rituximab, trastuzumab, and combinations thereof.

The use of CTLs and CAR-T cells as antigen-specific immunotherapeutic agents is a form of adoptive T cell transfer therapy. Adoptive T cell transfer therapy is a technique that can boost the natural immune system's ability to combat cancer and infectious diseases by enriching for and/or designing T cells that are able to effectively recognize, bind, and kill a diseased cell. CTLs can recognize and bind infected or cancerous cells using T-cell receptors (TCR). TCRs contain a highly variable binding region that allow them to recognize a large range of antigens. TCRs bind to the major histocompatibility complex I (MHC I) of infected or cancerous cells presenting an appropriate antigen. TCRs binding is highly specific, so only a small number of CTLs will be able to recognize a particular antigen. Once an antigen is recognized by CTLs binding to the MHC I complex of the infected cell, they activate to induce cellular death. Activated CTLs proliferate to fight the detected infection.

CTLs administered in this therapy may be derived from the subject or may be derived from other biological sources. Methods for producing CTLs directed to a particular antigen are well known in the art, and can be harvested from an individual possessing a CTL directed to a particular antigen or produced outside of the body (ex vivo). For example, when treating cancer, cytotoxic T cells from a subject's tumor are isolated, the cytotoxic T cells with the greatest antitumor activity are identified, the identified cytotoxic T cells are cultured to produce large amounts of the most effective cells, and the cultured cytotoxic T cells are reintroduced into the subject to treat the cancer. CTLs can also be produced in uninfected individuals using ex vivo techniques described in U.S. Pat. No. 5,962,318, and U.S. Patent Application Publication No. 2009/0324539, the contents of which are herein incorporated by reference for all purposes. When inducing CTLs for immunotherapy ex vivo, the antigen or antigens provided to the cell culture are chosen based on the disease or condition to be treated. Those that are most reactive with the antigen or antigens of choice can be cultured, and the CTLs produced can be reintroduced into the patient. Once reintroduced, the CTLs can recognize and kill the cancer cells. The ex vivo methods described herein can be useful for individuals both before infection/cancer onset or after infection/cancer onset. The same principle for producing CTLs in cancer treatment may be applied to infectious diseases.

CAR-T cells are modified T cells which have been engineered to possess a cellular specificity domain that has not been produced naturally. The natural specificity domain of T cells are T-cell receptors that recognize a particular antigen presented on MHC class I molecules. In some embodiments, CAR-T cells possess a T-cell receptor that has not been naturally produced in a subject's body. In some embodiments, the cellular specificity domain is a monoclonal antibody that is specific for the targeted cells or tissue. CAR-T cells can be produced using any means known in the art. In some embodiments, cytotoxic T cells are harvested from a subject's blood, the cytotoxic T cells are genetically modified by inserting a gene that encodes for a receptor that recognizes an antigen specific to the cancer or disease affecting the subject, the CAR-T cells are cultured and can be stored for later use or reintroduced into the subject's body to treat the disease. For more information on the details of producing CAR-T cells, see, e.g., U.S. Pat. No. 9,102,760, U.S. Pat. No. 8,399,645, U.S. Pat. No. 8,975,071, and U.S. Pat. No. 8,916,381, the contents of which are herein incorporated by reference for all purposes.

4. Endocrine Therapies

Endocrine therapy is the manipulation of the endocrine system through the administration of specific hormones or drugs which inhibit or decrease the production or activity of targeted hormones or alter the gene expression pattern of targeted cells. Endocrine therapy is particularly useful in certain types of cancer, including breast cancer. Any known hormone antagonist or modulator may be used in the present invention. Endocrine therapies useful in the present invention include, but are not limited to, aromatase inhibitors (e.g. letrozole), megestrol acetate, flutamide, tamoxifen, raloxifene, lasofoxifene, bazedoxifene, bazedoxifene/conjugated estrogens, and combinations thereof.

5. Tyrosine Kinase Inhibitors

Tyrosine kinase inhibitors are small molecules that inhibit tyrosine kinase proteins. Tyrosine kinases are enzymes that activate many proteins in cellular signal transduction cascades by addition of a phosphate group to the protein. High expression and aberrant activation, of tyrosine kinase proteins can cause undesirable "switching on" of cellular signaling pathways that can result in uncontrolled cellular proliferation associated with cancerous cellular phenotypes. Various forms of cancer are currently treated by inhibiting or reducing the activity of poorly regulated tyrosine kinase proteins with tyrosine kinase inhibitors. Treatment regimens with tyrosine kinase inhibitors can suppress, reduce the incidence, reduce the severity, or inhibit the progression of cancer. Examples of tyrosine kinase inhibitors include, but are not limited to, gefitinib, erlotinib, sorafenib, sunitinib, dasatinib, lapatinib, nilotinib, bortezomib, salinomycin, and combinations thereof.

6. Antimicrobial Agents

Antimicrobials are drugs, generally small molecules, that either kill microorganisms or inhibit their growth. Antimicrobials include antivirals, antibiotics, antifungals, and antiparasitic agents, all of which are well known in the art. In some embodiments, the TRIP compounds described herein are useful for boosting a subject's innate and adaptive immune responses while the antimicrobial agent acts directly on the infection. In certain instances, the patient overcomes the infection faster than using the antimicrobial agent alone. Without being bound by any particular theory, the basic principle for using antimicrobial agent treatment in combination with a TRIP compound for treating an infection in a subject in need thereof is that the antimicrobial agent knocks down the infection to the point where the subject's immune system is able to take over and eradicate the infection, and the TRIP compound augments this process by boosting the subject's innate and adaptive immune responses to eradicate the infection.

Antivirals are drugs used in treating viral infections, and generally function by inhibiting a particular step in the virus life cycle. Antiviral drugs typically target particular proteins associated with virus replication (e.g., reverse transcriptase) and are usually virus specific. A person of skill in the art can appropriately determine which known antiviral medication to apply based on the virus infecting the individual. In some embodiments, antivirals include viral integrase strand transfer inhibitors. In some embodiments, antivirals include viral nucleoside reverse transcriptase inhibitors. In some embodiments, antivirals include viral neuraminidase inhibitors. In some embodiments, antivirals used to treat HIV/AIDS infections include, but are not limited to, tenofovir, lamivudine, emtricitabine, efavirenz, emtricitabine, rilpivirine, fosamprenavir, ritonavir, darunavir, atazanavir, dolutegravir, zidovudine, abacavir, and combinations thereof. In some embodiments, antivirals used to treat filovirus infections, such as Ebola virus, include, but are not limited to, favipiravir, brincidofovir, 3-deazaneplanocin A, amiodarone, dronedarone, verapamil, and combinations thereof. In some embodiments, antivirals used to treat influenza include, but are not limited to, laninamivir, oseltamivir, peramivir, zanamivir, and combinations thereof.

Antibiotics are generally small molecules that can either kill or inhibit the growth of bacteria. The most common antibiotics are those that target the bacterial ribosome. Because the ribosome is ubiquitous, most antibiotics can treat many different types of bacteria. The increase in antibiotic resistance, however, may require the use of one or more antibiotics to treat the infection. Antibiotic classes include, but are not limited to, penicillins, cephalosporins, macrolides, fluoroquinolones, sulfonamides, tetracyclines, and aminoglycosides. A person of skill in the art can appropriately determine which known antibiotic medication to apply based on the bacteria infecting the individual. Examples of antibiotics used to treat bacterial infections include, but are not limited to, penicillin, amoxicillin, doxycycline, azithromycin, erythromycin, roxithromycin, ciprofloxacin, flucloxacillin, phenoxymethylpenicillin, benzylpenicillin, ceftriaxone, metronidazole, cefaclor, cefadroxil, cephalexin, tetracycline, lymecycline, gentamicin, tobramycin, co-trimoxazole, S-649266, and combinations thereof.

Antifungals are drugs that can kill or prevent the growth of fungi. Targets of antifungal drugs include sterol biosynthesis, DNA biosynthesis, and β-glucan biosynthesis. A person of skill in the art can appropriately determine which known antifungal medication to apply based on the fungus infecting the individual. Examples of common antifungals include, but are not limited to, amphotericin B, nystatin, fluconazole, itraconazole, ketoconazole, naftifine, and combinations thereof.

Antiparasitic agents are drugs that can kill or prevent the growth of the parasite. The most common parasites infecting individuals are helminthes and parasitic protozoa, each of which are treated with different types of antiparasitic agents. A person of skill in the art can determine the most appropriate antiparasitic agent to apply based parasite being treated. Antiparasitic agents include, but are not limited to, antihelminthic agents such as mebendazole, pyrantel pamoate, thiabendazole, diethylcarbamazine, niclosamide, praziquantel, albendazole, and combinations thereof. Antiparasitic agents also include, but are not limited to, antiprotozoal agents such as melarsoprol, eflornithine, metronidazole, tinidazole, miltefosine, and combinations thereof. A particularly prevalent disease caused by a parasitic infection is malaria. Antiparasitic agents further include, but are not limited to, antimalarial agents such as rufigallol, quinine and related agents, chloroquine, amodiaquine, pyrimethamine, proguanil, sulfonamides, mefloquine, atovaquone, primaquine, artemisinin and derivatives, halofantrine, doxycycline, clindamycin, and combinations thereof.

7. Thalidomide Derivatives

Thalidomide derivatives are immunomodulatory small molecules that are useful in the treatment of cancers and infectious diseases and certain complications that arise from infectious diseases. They modulate the immune system by altering the production of particular cytokines including TNF-α, IL-1, IL-6, IL-12, and IL-10, and have also been associated with the stimulation and activation of T-cells. Derivatives of thalidomide include, but are not limited to, thalidomide, lenalidomide, pomalidomide, apremilast, and combinations thereof.

In particular embodiments, thalidomide derivatives are beneficial in the treatment of CNS tuberculosis and conditions secondary to HIV and AIDS.

C. Diseases and Conditions

Administering a TRIP compound with a therapeutic agent is useful in treating or preventing many diseases including cancers and infectious diseases caused by, e.g., a virus, a bacterium, a fungus, a parasite, or any other infectious agent.

1. Cancer

In certain aspects, cancer can be treated or prevented by administering one or more TRIP compounds in combination with a therapeutic agent. Cancer generally includes any of various malignant neoplasms characterized by the proliferation of anaplastic cells that tend to invade surrounding tissue and metastasize to new body sites. Non-limiting examples of different types of cancer suitable for treatment using the compositions of the present invention include ovarian cancer, breast cancer, lung cancer (such as non-small-cell lung carcinoma), bladder cancer, thyroid cancer, liver cancer, pleural cancer, pancreatic cancer, cervical cancer, prostate cancer, testicular cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer (i.e., renal cell carcinoma), cancer of the central nervous system, skin cancer, choriocarcinomas, head and neck cancers, bone cancer, osteogenic sarcomas, fibrosarcoma, neuroblastoma, glioma, melanoma, leukemia (e.g., acute lymphocytic leukemia, chronic lymphocytic leukemia, acute myelogenous leukemia, chronic myelogenous leukemia, or hairy cell leukemia), lymphoma (e.g., non-Hodgkin's lymphoma, Hodgkin's lymphoma, B-cell lymphoma, or Burkitt's lymphoma), and multiple myeloma.

In particular embodiments, the cancer is lung cancer (e.g., non-small-cell lung carcinoma), melanoma, an epithelial cancer (e.g., prostate cancer, ovarian cancer, breast cancer), or a blood cancer (e.g., leukemia, lymphoma, multiple myeloma).

2. Infectious Disease

In certain other aspects, infectious diseases can be treated or prevented by administering one or more TRIP compounds in combination with a therapeutic agent. Infectious diseases that can be treated with compositions of the present invention include viral infections, bacterial infections, fungal infections, parasite infections, or any other infectious agent.

The virus treated with the compositions of the present invention can be any known virus including, but not limited to, Filoviruses such as Ebola virus and Marburg virus, Crimean-Congo hemorrhagic fever virus, Human immunodeficiency virus (HIV), Herpes simplex, type 1, Herpes simplex, type 2, Human herpesvirus, type 8, Hepatitis A virus, Hepatitis B virus, Hepatitis C virus, Hepatitis D virus, Hepatitis E virus, Influenza virus, Parainfluenza virus, yellow fever virus, *Varicella zoster* virus, West Nile virus, dengue virus, Rabies virus, Measles virus, Mumps virus, poliovirus, Smallpox, Epstein-Barr virus, Human cytomegalovirus, Junin virus, Adenovirus, Orbivirus, Banna virus, Guanarito virus, Lassa virus, Rubella virus, JC virus, Machupo virus, Parvovirus B19, Hendra virus, Severe acute respiratory syndrome virus, Respiratory syncytial virus, BK virus, rhinovirus, coxsackievirus, Human papillomavirus, Norwalk virus, Human astrovirus, Human bocavirus, Human metapneumovirus, Rotavirus, Coltivirus, Sabiá virus, and Nipah virus.

In particular embodiments, the TRIP compounds described herein are useful for the treatment of Ebola virus, and improving the immune response to vaccines such as the seasonal flu vaccine (influenza), the shingles vaccine used to prevent flare ups caused by the *Varicella zoster* virus, the pneumococcal vaccines PCV13 (pneumococcal conjugate vaccine 13-valent), and PPSV23 (pneumococcal polysaccharide vaccine 23-valent) used to prevent infections caused by numerous strains of the bacterium *Streptococcus pneumoniae*, and Tdap vaccine used to prevent tetanus, diphtheria and pertussis infections. In some embodiments, the TRIP compounds described herein are useful in boosting the immune response in individuals 50 and older, particularly those 65 and older.

The bacterial infection treated with the compositions of the present invention can be any known bacterium including, but not limited to, *Streptococcus pneumoniae*, tubercle bacilli, *Bacillus anthraces, Escherichia coli, Salmonella typhimurium, Salmonella typhi, Salmonella thyphosa, Yersinia pestis, Vibrio cholerae, Clostridium perfringens, staphylococcus, Pseudomonas aeruginosa, Shigella, Klebsiella, Haemophilus influenzae, Pasteurella, Actinobacillus, Legionella, Bordetella pertussis, Francisella tularensis, Brucella, Vibrio parahaemolyticus, Neisseria gonorrhoeae, Neisseria meningitidis, Helicobacter pylori, Spirillum minus, Borrelia recurrentis, Borrelia burgdoferi, Clostridium tetani, Mycobacterium leprae*, and *Mycobacterium lepromatosis*.

The parasitic infection treated with the compositions of the present invention can be any known parasite including, but not limited to, *Plasmodium, Schistosoma, Ascaris, Dracunculus Babesia, Toxoplasma, Eimeria, Isospora, Atoxoplasma, Cystoisospora, Hammondia, Besniotia, Sarcocystis, Frenkelia, Haemoproteus, Leucocytozoon, Theileria, Perk-*

*insus, Nosema, Enterocytozoon, Encephalitozoon, E. intestinalis, Mrazekia, Amblyospora, Arneson, Glugea,* and *Pleistophora.*

The fungal infection treated with the compositions of the present invention can be any known fungus including, but not limited to, *Aspergillus, Blastomyces dermatitides, Candida albicans, Coccidioides, Cryptococcus neoformans, Cryptococcus gattii, Histoplasma capsulatum, Mucoromycotina, Pneumocystis jirovecii, Sporothrix schenckii,* and *Exserohilum.*

D. Pharmaceutical Compositions

The TRIP compounds described herein are useful in the manufacture of a pharmaceutical composition or a medicament for modulating the immune system of a subject with cancer or an infectious disease. In certain aspects, a pharmaceutical composition or medicament comprising one or more TRIP compounds can be administered to a subject for the treatment of a cancer or infectious disease in combination with a therapeutic agent to enhance the immune response of the subject to the therapeutic agent.

Pharmaceutical compositions or medicaments for use in the present invention can be formulated by standard techniques or methods well-known in the art of pharmacy using one or more physiologically acceptable carriers or excipients. Suitable pharmaceutical carriers are described herein and in, e.g., "Remington's Pharmaceutical Sciences" by E. W. Martin. Compounds and agents of the present invention and their physiologically acceptable salts and solvates can be formulated for administration by any suitable route, including, but not limited to, orally, topically, nasally, rectally, pulmonary, parenterally (e.g., intravenously, subcutaneously, intramuscularly, etc.), and combinations thereof. In some embodiments, the TRIP compound is dissolved in a liquid, for example, water. The most suitable route of administration for a TRIP compound or a therapeutic agent in any given case will depend, in part, on the type of therapeutic agent being used as well as the nature, severity, and optionally, the stage of the cancer or infectious disease. In embodiments where the TRIP compound is administered in combination with a therapeutic agent, the administration of the TRIP compound and the therapeutic agent may be administered using the same or a different administration route. For example, in some embodiments, the TRIP compound may be administered orally, while the therapeutic agent may be administered subcutaneously.

The pharmaceutical compositions or medicaments of the present invention can include one or more TRIP compounds with one or more therapeutic agents or any pharmaceutically acceptable salts thereof, as an active ingredient and a pharmaceutically acceptable carrier and/or excipient or diluent. In some embodiments, the pharmaceutical compositions comprising a TRIP compound and the pharmaceutical compositions comprising a therapeutic agent are prepared as separate medicaments. In some embodiments, the pharmaceutical compositions comprising a TRIP compound and the pharmaceutical compositions comprising a therapeutic agent are prepared as a single medicament.

In embodiments where more than one TRIP compound is used, the TRIP compounds can be combined as the active ingredient in intimate admixture with a suitable pharmaceutical carrier and/or excipient according to conventional pharmaceutical compounding techniques. Any carrier and/or excipient suitable for the form of preparation desired for administration is contemplated for use with the compounds disclosed herein.

In certain embodiments, the pharmaceutical compositions or medicaments described herein are suitable for systemic administration. Systemic administration includes enteral administration (e.g., absorption of the compound through the gastrointestinal tract) or parenteral administration (e.g., injection, infusion, or implantation). In some embodiments, the pharmaceutical compositions or medicaments may be administered via a syringe or intravenously. In preferred embodiments, the pharmaceutical compositions or medicaments are injected subcutaneously.

In some embodiments, the present invention provides a pharmaceutical composition including a TRIP compound, a chemotherapeutic agent, and a pharmaceutically acceptable excipient. In some embodiments, the TRIP compound and the chemotherapeutic agent are separately prepared pharmaceutical compositions. In some embodiments, the pharmaceutically acceptable excipient includes a salt or a diluent.

In some embodiments, the present invention provides a pharmaceutical composition including a TRIP compound, a radiotherapeutic agent, and a pharmaceutically acceptable excipient. In some embodiments, the TRIP compound and the radiotherapeutic agent are separately prepared pharmaceutical compositions. In some embodiments, the pharmaceutically acceptable excipient includes a salt or a diluent.

In some embodiments, the present invention provides a pharmaceutical composition including a TRIP compound, a vaccine, and a pharmaceutically acceptable excipient. In some embodiments, the TRIP compound and the vaccine are separately prepared pharmaceutical compositions. In some embodiments, the pharmaceutically acceptable excipient includes a salt or a diluent.

In some embodiments, the present invention provides a pharmaceutical composition including a TRIP compound, an antibody, and a pharmaceutically acceptable excipient. In some embodiments, the TRIP compound and the antibody are separately prepared pharmaceutical compositions. In some embodiments, the pharmaceutically acceptable excipient includes a salt or a diluent.

In some embodiments, the present invention provides a pharmaceutical composition including a TRIP compound, cytotoxic T cells, and a pharmaceutically acceptable excipient. In some embodiments, the TRIP compound and the cytotoxic T cells are separately prepared pharmaceutical compositions. In some embodiments, the pharmaceutically acceptable excipient includes a salt or a diluent.

In some embodiments, the present invention provides a pharmaceutical composition including a TRIP compound, chimeric antigen receptor T cells, and a pharmaceutically acceptable excipient. In some embodiments, the TRIP compound and the chimeric antigen receptor T cells are separately prepared pharmaceutical compositions. In some embodiments, the pharmaceutically acceptable excipient includes a salt or a diluent.

In some embodiments, the present invention provides a pharmaceutical composition including a TRIP compound, an endocrine therapy, and a pharmaceutically acceptable excipient. In some embodiments, the TRIP compound and the endocrine therapy are separately prepared pharmaceutical compositions. In some embodiments, the pharmaceutically acceptable excipient includes a salt or a diluent.

In some embodiments, the present invention provides a pharmaceutical composition including a TRIP compound, a tyrosine kinase inhibitor, and a pharmaceutically acceptable excipient. In some embodiments, the TRIP compound and the tyrosine kinase inhibitor are separately prepared pharmaceutical compositions. In some embodiments, the pharmaceutically acceptable excipient includes a salt or a diluent.

In some embodiments, the present invention provides a pharmaceutical composition including a TRIP compound, a antimicrobial agent, and a pharmaceutically acceptable excipient. In some embodiments, the TRIP compound and the antimicrobial agent are separately prepared pharmaceutical compositions. In some embodiments, the pharmaceutically acceptable excipient includes a salt or a diluent.

For oral administration, a pharmaceutical composition or a medicament can take the form of, e.g., a tablet or a capsule prepared by conventional means with a pharmaceutically acceptable excipient. Preferred are tablets and gelatin capsules comprising the active ingredient(s), together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, anhydrous colloidal silica, talcum, stearic acid, its magnesium or calcium salt (e.g., magnesium stearate or calcium stearate), metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulfate, and/or (f) absorbents, colorants, flavors and sweeteners. In some embodiments, the tablet contains a mixture of hydroxypropyl methylcellulose, polyethyleneglycol 6000 and titatium dioxide. Tablets may be either film coated or enteric coated according to methods known in the art.

Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

Pharmaceutical compositions for pulmonary administration include, but are not limited to, dry powder compositions consisting of the powder of a compound described herein, or a salt thereof, and the powder of a suitable carrier and/or lubricant. The compositions for pulmonary administration can be inhaled from any suitable dry powder inhaler device known to a person skilled in the art. In certain instances, the compositions may be conveniently delivered in the form of an aerosol spray from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound(s) and a suitable powder base, for example, lactose or starch.

The TRIP compounds and the therapeutic agents can also be formulated in rectal compositions, for example, suppositories or retention enemas, for example, containing conventional suppository bases, for example, cocoa butter or other glycerides.

The compositions set forth herein can be formulated for parenteral administration by injection, for example by bolus injection. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the compound(s) can be in powder form for reconstitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the compound(s).

In some embodiments, the compounds are prepared with a polysaccharide such as chitosan or derivatives thereof (e.g., chitosan succinate, chitosan phthalate, etc.), pectin and derivatives thereof (e.g., amidated pectin, calcium pectinate, etc.), chondroitin and derivatives thereof (e.g., chondroitin sulfate), and alginates.

In some embodiments, the compositions further include a pharmaceutical surfactant. In other embodiments, the compositions further include a cryoprotectant. Non-limiting examples of cryoprotectants include glucose, sucrose, trehalose, lactose, sodium glutamate, PVP, cyclodextrin, 2-hydroxypropyl-13-cyclodextrin (HPI3CD) glycerol, maltose, mannitol, saccharose, and mixtures thereof.

E. Methods of Administration

Pharmaceutical compositions or medicaments comprising a TRIP compound can be administered to a subject at a therapeutically effective dose in combination with an effective amount of a therapeutic agent to modulate the subject's immune system, as described herein. In some embodiments, the pharmaceutical composition or medicament comprising a TRIP compound is administered to a subject in an amount sufficient in combination with an effective amount of a therapeutic agent to elicit an effective therapeutic response in the subject. In some embodiments, the pharmaceutical composition or medicament comprising a TRIP compound can be administered to a subject at a therapeutically effective dose in combination with an effective amount of a therapeutic agent to elicit improved T cell response. In some embodiments, the pharmaceutical composition or medicament comprising a TRIP compound can be administered in combination with an effective amount of a therapeutic agent to a subject at a therapeutically effective dose to augment the innate T cell immune response. In some embodiments, the pharmaceutical composition or medicament comprising a TRIP compound can be administered to a subject at a therapeutically effective dose in combination with an effective amount of a therapeutic agent to decrease inflammation. In some embodiments, the pharmaceutical composition or medicament comprising a TRIP compound can be administered to a subject at a therapeutically effective dose in combination with an effective amount of a therapeutic agent to inhibit T regulatory cell activity.

The combination therapy described herein includes simultaneous administration as well as sequential administration. In some embodiments, the pharmaceutical composition or medicament comprising a TRIP compound is administered in a different time regiment than the therapeutic agent. As a non-limiting example, the pharmaceutical composition or medicament may be administered daily, while the therapeutic agent may be administered weekly, or the pharmaceutical composition or medicament may be administered weekly, while the therapeutic agent is administered daily.

The pharmaceutical composition or medicament comprising a TRIP compound may be administered on a routine schedule (e.g., hourly, daily, every 3 days, weekly, monthly, yearly) or according to a cyclic schedule (e.g., 1 week of daily administration, 2 consecutive weeks without administration, or 3 consecutive weeks of daily administration, 3 consecutive weeks without administration, or 4 consecutive weeks of daily administration, 5 consecutive weeks without administration, and repeating the cycles as necessary). The therapeutic agent may also be administered on a routine or cyclic schedule, or at time intervals generally recommended for each therapeutic agent. In embodiments where the composition or medicament comprising a TRIP compound and/or the therapeutic agent is administered on a cyclic schedule, the time interval of consecutive daily administration can include 1 day, 2 days, 3 days, 4 days, 5 days, 6 days, 7 days, 2 weeks, 3, weeks, 4 weeks, or 2 months, and the time intervals of not administering a TRIP compound or a therapeutic agent can include 1 day, 2 days, 3 days, 4 days, 5 days, 6 days, 7 days, 2 weeks, 3, weeks, 4 weeks, 2 months, 3 months, 4 months, 5 months, 6 months, or a year wherein the days of successive administration and non-administration are independently selected.

In some embodiments, the timing of sequential administration of one or more TRIP compounds and one or more therapeutic agents is dependent on predetermined cytokine levels of a subject. In some embodiments, one or more TRIP compounds are administered to a subject, and predetermined cytokine levels of the subject are monitored. When the predetermined cytokine levels of a subject receiving doses of one or more TRIP compounds have reached a certain (threshold) level or have returned to a certain (baseline) level, the therapeutic agent can be administered. Non-limiting examples of predetermined cytokine levels that can be determined include one or more of IL-2, IL-12, IFN-γ, TNF-α, IL-4, IL-5, IL-10, IL-13, MIP-1α, IP-10 (interferon gamma-induced protein 10), MIG (interferon gamma-induced protein 10), IL-1β, IL-6, KC (keratinocyte derived cytokine), and combinations thereof. In certain embodiments, the predetermined cytokine biomarker level determined is IFN-γ.

In some embodiments, one or more TRIP compounds (e.g., compounds of Formula I such as ospemifene, fispemifene, or analogs thereof) are administered in combination with a therapeutic agent to a patient with cancer or an infectious disease to enhance the immune response of the subject.

In some embodiments, one or more TRIP compounds (e.g., compounds of Formula I such as ospemifene, fispemifene, or analogs thereof) are administered in combination with a chemotherapeutic agent to a patient with cancer to enhance the immune response of the subject.

In some embodiments, one or more TRIP compounds (e.g., compounds of Formula I such as ospemifene, fispemifene, or analogs thereof) are administered in combination with a radiotherapeutic agent to a patient with cancer or an infectious disease to enhance the immune response of the subject.

In some embodiments, one or more TRIP compounds (e.g., compounds of Formula I such as ospemifene, fispemifene, or analogs thereof) are administered in combination with an antigen-specific immunotherapeutic agent to a patient with cancer or an infectious disease to enhance the immune response of the subject.

In some embodiments, one or more TRIP compounds (e.g., compounds of Formula I such as ospemifene, fispemifene, or analogs thereof) are administered in combination with an endocrine therapy (e.g., letrozole) to a patient with cancer or an infectious disease to enhance the immune response of the subject.

In some embodiments, one or more TRIP compounds (e.g., compounds of Formula I such as ospemifene, fispemifene, or analogs thereof) are administered in combination with a tyrosine kinase inhibitor (e.g., lapatinib) to a patient with cancer or an infectious disease to enhance the immune response of the subject.

In some embodiments, one or more TRIP compounds (e.g., compounds of Formula I such as ospemifene, fispemifene, or analogs thereof) are administered in combination with an antimicrobial agent to a patient with cancer or an infectious disease to enhance the immune response of the subject.

In particular embodiments, one or more TRIP compounds (e.g., compounds of Formula I such as ospemifene, fispemifene, or analogs thereof) are administered in combination with a fluoroquinolone antibiotic (e.g., ciprofloxacin) and/or a cephalosporin antibiotic (e.g., ceftriaxone) for the treatment of pneumococcal pneumonia. In certain instances, the treatment is administered to patients over the age of 50.

In particular embodiments, one or more TRIP compounds (e.g., compounds of Formula I such as ospemifene, fispemifene, or analogs thereof) are administered in combination with an HIV integrase strand transfer inhibitor (e.g., dolutegravir) for the treatment of HIV/AIDS.

In particular embodiments, one or more TRIP compounds (e.g., compounds of Formula I such as ospemifene, fispemifene, or analogs thereof) are administered in combination with an HIV integrase strand transfer inhibitor (e.g., dolutegravir) and a nucleoside reverse transcriptase inhibitor (e.g., abacavir or lamivudine) for the treatment of HIV/AIDS.

In particular embodiments, one or more TRIP compounds (e.g., compounds of Formula I such as ospemifene, fispemifene, or analogs thereof) are administered in combination with a neuraminidase inhibitor (e.g., peramivir) for the treatment of influenza.

In some embodiments, one or more TRIP compounds (e.g., compounds of Formula I such as ospemifene, fispemifene, or analogs thereof) are administered in combination with a cephalosporin antibiotic (e.g., S-649266) for the treatment of *Pseudomonas* infections.

In some embodiments, one or more TRIP compounds (e.g., compounds of Formula I such as ospemifene, fispemifene, or analogs thereof) are administered in combination with a vaccine (e.g., peptide vaccine) to a patient with cancer or an infectious disease to enhance the immune response of the subject.

In particular embodiments, one or more TRIP compounds (e.g., compounds of Formula I such as ospemifene, fispemifene, or analogs thereof) are administered in combination with a pneumococcal vaccine (e.g., PCV13 vaccine) for the prevention of pneumococcal disease. In certain instances, the treatment is administered to patients over the age of 50.

In particular embodiments, one or more TRIP compounds (e.g., ospemifene, fispemifene, or analogs thereof) are administered in combination with an Ebola vaccine (e.g., VSV-EBOV vaccine) for the prevention and treatment of Ebola virus disease.

In particular embodiments, one or more TRIP compounds (e.g., compounds of Formula I such as ospemifene, fispemifene, or analogs thereof) are administered in combination with a cancer vaccine (e.g., tecemotide (L-BLP25)) and/or an immune checkpoint inhibitor (e.g., nivolumab) following primary chemoradiotherapy (e.g., a chemotherapeutic agent such as cisplatin and a radiotherapeutic agent such as external beam radiation therapy) for the treatment of non-small cell lung cancer (NSCLC).

In particular embodiments, one or more TRIP compounds (e.g., compounds of Formula I such as ospemifene, fispemifene, or analogs thereof) are administered in combination with an immune checkpoint inhibitor (e.g., nivolumab) and one or more chemotherapeutic agents (e.g., carboplatin and paclitaxel) for the treatment of ovarian cancer.

In particular embodiments, one or more TRIP compounds (e.g., compounds of Formula I such as ospemifene, fispemifene, or analogs thereof) are administered in combination with chemoradiotherapy (e.g., a chemotherapeutic agent such as cisplatin and a radiotherapeutic agent such as external beam radiation therapy) for the treatment of breast cancer. In certain embodiments, an immune checkpoint inhibitor (e.g., atezolizumab) is also administered in combination with one or more TRIP compounds and chemoradiotherapy for the treatment of breast cancer.

In particular embodiments, one or more TRIP compounds (e.g., compounds of Formula I such as ospemifene, fispemifene, or analogs thereof) are administered in combination with an endocrine therapy such as tamoxifen or a metabolite thereof for the treatment of breast cancer.

In some embodiments, the methods to modulate the immune system described herein are administered to a subject at risk of developing a cancer or contracting an infectious disease. In certain embodiments, the therapeutic agent used is a peptide vaccine. In some embodiments, cytotoxic T lyphocytes are harvested from an at risk subject and stored for later administration to the subject if the subject develops the cancer or contracts the infectious disease. In some embodiments, the cytotoxic T lymphocytes produced by the subject in this method are harvested from the at risk subject, genetically modified to CAR-T cells as described herein, and stored for later administration to the subject if the subject develops the cancer or contracts the infectious disease. In some embodiments, cytotoxic T lymphocytes of at risk individuals are produced ex vivo, as described herein.

In some embodiments, the methods to modulate the immune system described herein are adminstered to a subject with a cancer or an infectious disease. In certain embodiments, the therapeutic agent is an antigen specific immunotherapeutic agent, a chemotherapeutic agent, a radiotherapeutic agent, an endocrine therapy, a tyrosine kinase inhibitor or combinations thereof.

The formulations of the present invention are useful in the manufacture of a pharmaceutical composition or a medicament. A pharmaceutical composition or medicament can be administered to a subject in need thereof, e.g. a patient with cancer or a patient having a viral infection, bacterial infection, parasitic infection, fungal infection, or infected with any other infectious agent.

In certain methods of modulating the immune system, set forth herein, the methods comprise first administering a TRIP compound to a patient with cancer or an infectious disease, and then administering a therapeutic agent to the patient. In certain methods of modulating the immune response, set forth herein, the methods comprise first administering a therapeutic agent to a patient with cancer or an infectious disease, and then administering a TRIP compound to the patient. In certain other methods of modulating the immune system, a TRIP compound and a therapeutic agent are administered simultaneously to a patient with cancer or an infectious disease.

In some embodiments, the TRIP compound is administered in different dosing schedules to provide a biphasic immunomodulation effect, meaning that the TRIP compound can induce different immune responses dependent on the amount of the TRIP compound administered. The biphasic activity of the TRIP compounds makes them useful as immunomodulators for treating cancer and infectious disease. In some embodiments, a high dosing regimen of a TRIP compound enhances a subject's T cell response. In some embodiments, a low dosing regimen of a TRIP compound reduces inflammation. For example, different dose schedules of TRIP compounds can be employed such that when used sequentially, one dose enhances the T cell response, followed by a different dose that decreases inflammation to enhance treatment response to a therapeutic agent.

In certain methods of modulating the immune system, set forth herein, the methods comprise:
(a) administering a first dosing regimen of an effective amount of a TRIP compound (e.g., compound of Formula I) in combination with an effective amount of a first therapeutic agent to the subject, wherein the effective amount of the TRIP compound (e.g., compound of Formula I) is an amount sufficient to enhance the T cell response to the first therapeutic agent; and
(b) administering a second dosing regimen of an effective amount of the TRIP compound (e.g., compound of Formula I) in combination with an effective amount of a second therapeutic agent to the subject, wherein the effective amount of the TRIP compound (e.g., compound of Formula I) is an amount sufficient to decrease inflammation and enhance the response to the second therapeutic agent.

The administration of the TRIP compound and the first therapeutic agent in the first dosing regimen and the administration of the TRIP compound and the second therapeutic agent in the second dosing regimen described herein may be simultaneous or sequential, as described above. The first and second dosing regimen may also be administered according to a routine schedule or a cyclic schedule, as described above. For example, a first dosing regimen may include daily doses of a TRIP compound, while a second dosing regimen may include doses of a TRIP compound administered every other day. Upon completion of the first dosing regimen there may be a gap of 1 day, 2 days, 3 days, 4 days, 5 days, 6 days, 7 day, 1 week, or 2 weeks before beginning the second dosing regimen.

In some embodiments, the first therapeutic agent is an antigen-specific immunotherapeutic agent. In some embodiments the antigen-specific immunotherapeutic agent is a vaccine, preferably a peptide vaccine. In some embodiments the antigen-specific immunotherapeutic agent is an antibody. In some embodiments the antigen-specific immunotherapeutic agent is a cytotoxic T cell lymphocyte. In some embodiments the antigen-specific immunotherapeutic agent is chimeric antigen receptor T cell.

In some embodiments, the second therapeutic agent is a chemotherapeutic agent. In some embodiments, the second therapeutic agent is a radiotherapeutic agent. In some embodiments, the second therapeutic agent is an endocrine therapy. In some embodiments, the second therapeutic agent is an antibody. In some embodiments, the second therapeutic agent is a tyrosine kinase inhibitor.

In some embodiments the first dosing regimen is administered before the first therapeutic agent. In some embodiments the first and second dosing regimens are administered sequentially.

F. Dosage

Pharmaceutical compositions or medicaments comprising a TRIP compound and a therapeutic agent can be administered to a subject suffering from a cancer or infectious disease at a therapeutically effective dose to enhance the immune response as described herein. The pharmaceutical compositions or medicaments are administered to a subject in an amount sufficient to elicit an effective therapeutic response in the subject.

The dosage of compounds administered is dependent on the subject's body weight, age, individual condition, and/or on the form of administration. The size of the dose will also be determined by the existence, nature, and extent of any adverse effects that accompany the administration of a particular compound in a particular subject. Typically, a dosage of the active compounds is a dosage that is sufficient to achieve the desired effect. Optimal dosing schedules can be calculated from measurements of compound accumulation in the body of a subject. In general, dosage may be given once or more daily, weekly, or monthly. Persons of ordinary skill in the art can easily determine optimum dosages, dosing methodologies, and repetition rates.

The effective amount of a therapeutic agent administered with a TRIP compound may be provided at the dosages generally recommended for each therapeutic agent used. In some instances it may be necessary to increase or decrease the dosage levels to achieve the desired effect. For instance, some therapeutic agents when administered with TRIP compounds may be effective at a lower dose. Optimal dosing schedules can be determined from measurements of compound accumulation in the body of a subject. Persons of ordinary skill in the art can easily determine optimum dosages, dosing methodologies, and repetition rates to optimize the effect of each therapeutic agent.

In some embodiments, a unit dosage for oral administration of a TRIP compound to a subject (e.g., a human) of about 50 to about 70 kg may contain between about 1 and about 500 mg, about 5 and about 500 mg, about 5 and about 250 mg, about 25 to about 250 mg, about 100 and about 1000 mg, about 200 and about 2000 mg, about 500 and about 5000 mg, or about 1000 and about 2000 mg of the compound(s). In particular embodiments, a unit dosage for oral administration of a TRIP compound to a subject (e.g., human) of about 50 to about 70 kg may contain about 5 mg, 10 mg, 15 mg, 20 mg, 25 mg, 30 mg, 35 mg, 40 mg, 45 mg, 50 mg, 75 mg, 100 mg, 200 mg, 300 mg, 400 mg, 500 mg, 600 mg, 700 mg, 800 mg, 900 mg, 1000 mg, 1250 mg, 1500 mg, 2000 mg, 2500 mg, 3000 mg, or more of the compound(s).

In some embodiments, a unit dosage for subcutaneous administration of a TRIP compound to a subject (e.g., human) of about 50 to about 70 kg may contain between about 0.1 and about 100 mg, about 0.5 and about 100 mg, about 0.5 and about 50 mg, about 0.5 and about 25 mg, about 0.5 and about 10 mg, about 0.25 to about 50 mg, about 0.25 to about 25 mg, about 0.1 to about 50 mg, about 0.1 to about 25 mg, or about 0.1 to about 10 mg of the compound(s). In particular embodiments, a unit dosage for subcutaneous administration of a TRIP compound to a subject (e.g., human) of about 50 to about 70 kg may contain about 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, 45 mg, 50 mg, 75 mg, 100 mg, or more of the compound(s).

The methods described herein sometimes include a first and second dosing regimen. In some embodiments, the first dosing regimen comprises a high dose of a TRIP compound, and the second dosing regimen comprises a low dose of the TRIP compound. The high dosing regimen may increase T cell response, while the low dosing regimen may reduce inflammation and increase the therapeutic benefit of the therapeutic agent being administered. Examples of a high dosing regimen of an oral dose of a TRIP compound include, but are not limited to, about 500 mg, 600 mg, or 700 mg per day administered to a 50-70 kg individual. Examples of a low dosing regimen of an oral dose of a TRIP compound include, but are not limited to, about 50 mg, 60 mg, 70 mg, or 100 mg per day administered to a 50-70 kg individual.

When one or more of the compositions is to be administered to a mammal, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific composition employed, the age, body weight, general health, gender, and diet of the subject, the time of administration, the route of administration, the rate of excretion, any drug combination, and the degree of expression or activity to be modulated.

In some embodiments, a pharmaceutical composition or medicament of the present invention is administered orally, e.g., in a dose in the range of from about 1 to about 1000 micrograms (µg) of compound per kg of subject body weight, from about 1 to about 500 µg/kg body weight, from about 10 to about 1000 µg/kg body weight, from about 10 to about 500 µg/kg body weight, from about 50 to about 1000 µg/kg body weight, from about 50 to about 500 µg/kg body weight, from about 100 to about 1000 µg/kg body weight, or from about 100 to about 500 µg/kg body weight. In particular embodiments, the dose is about 10, 25, 50, 75, 100, 200, 300, 400, 500, 600, 700, 800, 900, or 1000 µg/kg body weight. The dose can be administered once per day or divided into sub-doses and administered in multiple doses, e.g., twice, three times, or four times per day. However, as will be appreciated by a skilled artisan, oral compositions described herein may be administered in different amounts and at different times.

In some embodiments, a pharmaceutical composition or medicament of the present invention is administered subcutaneously, e.g., in a dose in the range of from about 1 to about 500 micrograms (µg) of compound per kg of subject body weight, from about 1 to about 200 µg/kg body weight, from about 1 to about 100 µg/kg body weight, from about 10 to about 500 µg/kg body weight, from about 10 to about 200 µg/kg body weight, from about 10 to about 100 µg/kg body weight, or from about 10 to about 80 µg/kg body weight. In particular embodiments, the dose is about 1, 5, 10, 15, 20, 25, 30, 35, 40, 45, 50, 55, 60, 65, 70, 75, 80, 85, 90, 95, 100, 200, 300, 400, or 500 µg/kg body weight. The dose can be administered once per day or divided into sub-doses and administered in multiple doses, e.g., twice, three times, or four times per day. However, as will be appreciated by a skilled artisan, subcutaneous compositions described herein may be administered in different amounts and at different times.

In some embodiments, the compounds are administered for about 1 to about 31 days, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. In some embodiments, the compounds are administered for at least 1 day. In other embodiments, the compounds are administered for one or more weeks, e.g., 1, 2, 3, 4, 5, 6, 7, 8, 9, 10, 11, 12, 13, 14, or more weeks. In yet other embodiments, the compounds are administered for one or more months, e.g., 1, 2, 3, 4, 5, 6, 7, 8, 9, 10, 11, 12, or more months.

In particular embodiments, the TRIP compounds described herein are administered in accordance with a short-course dosing or treatment regimen. In certain instances, short-course TRIP treatment enhances the immune response to a therapeutic agent such as an antigen-specific therapy (e.g., peptide vaccine) in a subject having or at risk of developing cancer or an infectious disease. In some instances, a low dose of one or more TRIP compounds is administered in accordance with the short-course dosing or treatment regimen. In other instances, a high dose of one or more TRIP compounds is administered in accordance with the short-course dosing or treatment regimen.

To achieve the desired therapeutic effect, compounds may be administered for multiple days at the therapeutically effective daily dose. Thus, therapeutically effective administration of compounds to treat a pertinent condition or disease described herein in a subject requires periodic (e.g., daily or twice daily) administration that continues for a period ranging from three days to two weeks or longer. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every day, every other day, or, if higher dose ranges are employed and tolerated by the subject, twice a week.

Optimum dosages, toxicity, and therapeutic efficacy of such compounds may vary depending on the relative potency of individual compounds and can be determined by standard pharmaceutical procedures in experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While compounds that exhibit toxic side-effects can be used, care should be taken to design a delivery system that targets such compounds to the affected site to minimize potential damage to normal cells and, thereby, reduce side-effects.

The data obtained from, for example, animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration.

A dose can be formulated in animal models to achieve a concentration range that includes the $IC_{50}$ (the concentration of the agent that achieves a half-maximal inhibition of symptoms) as determined in cell culture. Such information can be used to more accurately determine useful doses in humans. Levels in stool or an enteric tissue sample can be measured, for example, by high performance liquid chromatography (HPLC). In general, the dose equivalent of compounds is from about 1 ng/kg to about 500 mg/kg for a typical subject.

The dosage of a pharmaceutical composition or medicament of the present invention can be monitored and adjusted throughout treatment, depending on severity of symptoms, frequency of recurrence, and/or the physiological response to the therapeutic regimen. Those of skill in the art commonly engage in such adjustments in therapeutic regimens.

Single or multiple administrations of the pharmaceutical compositions or medicaments can be administered depending on the dosage and frequency as required and tolerated by the patient. In any event, the composition or medicament should provide a sufficient quantity of the compounds of the invention to effectively treat the patient. Generally, the dose is sufficient to enhance the immune response without producing unacceptable toxicity or side-effects to the patient.

G. Kits, Containers, Devices, and Systems

A wide variety of kits and systems can be prepared according to the present invention, depending upon the intended user of the kit and system and the particular needs of the user. In some aspects, the present invention provides a kit that includes one or more TRIP compounds and one or more therapeutic agents selected from a chemotherapeutic agent, a radiotherapeutic agent, an antigen-specific immunotherapeutic agent, an endocrine therapy, a tyrosine kinase inhibitor, a thalidomide derivative, and combinations thereof. In other aspects, the present invention provides a kit that includes one or more TRIP compounds and one or more therapeutic agents selected from an antigen-specific immunotherapeutic agent, an antiviral, an antibiotic, and antifungal, a thalidomide derivative, and combinations thereof. In certain embodiments, the kit includes a TRIP compound and a chemotherapeutic agent.

Some of the kits described herein include a label describing a method of administering one or more TRIP compounds and/or one or more therapeutic agents described herein. Some of the kits described herein include a label describing a method of enhancing the immune response of a subject with a cancer or infectious disease.

The compositions of the present invention, including but not limited to, compositions comprising one or more TRIP compounds and one or more therapeutic agents described herein may, if desired, be presented in a bottle, jar, vial, ampoule, tube, or other container-closure system approved by the Food and Drug Administration (FDA) or other regulatory body, which may provide one or more dosages containing the compounds. The package or dispenser may also be accompanied by a notice associated with the container in a form prescribed by a governmental agency regulating the manufacture, use, or sale of pharmaceuticals, the notice indicating approval by the agency. In certain aspects, the kit may include a formulation or composition as described herein, a container closure system including the formulation or a dosage unit form including the formulation, and a notice or instructions describing a method of use as described herein.

In some embodiments, the kit includes a container which is compartmentalized for holding the various elements of a formulation (e.g., the dry ingredients and the liquid ingredients) or composition, instructions for making the formulation or composition, and instructions for administering the formulation or composition for enhancing the immune response in a subject with a cancer or infectious disease.

In some embodiments, the instructions include timing information on when to sequentially administer one or more TRIP compounds and one or more therapeutic agents. In some embodiments, the one or more TRIP compounds are administered to a subject, and predetermined cytokine levels are monitored in the subject. When the predetermined cytokine levels have reached a certain (threshold) level or have returned to a certain (baseline) level, the therapeutic agent can be administered. Non-limiting examples of predetermined cytokine levels that can be determined include one or more of IL-2, IL-12, IFN-γ, TNF-α, IL-4, IL-5, IL-10, IL-13, MIP-1α, IP-10 (interferon gamma-induced protein 10), MIG (interferon gamma-induced protein 10), IL-1β, IL-6, KC (keratinocyte derived cytokine), and combinations thereof. In certain embodiments, the predetermined cytokine level determined is IFN-γ.

In certain embodiments, the kit may include the pharmaceutical preparation in dehydrated or dry form, with instructions for its rehydration (or reconstitution) and administration.

Kits with unit doses of the compounds described herein, e.g. in oral, rectal, transdermal, or injectable doses (e.g., for intramuscular, intravenous, or subcutaneous injection), are provided. In such kits, an informational package insert describing the use and attendant benefits of the composition for enhancing the immune response in a subject with a cancer or infectious disease may be included in addition to the containers containing the unit doses.

Some embodiments of the present invention include packages that include one or more TRIP compounds and one or more therapeutic agents described herein.

IV. Examples

The following examples are offered to illustrate, but not to limit, the claimed invention.

In particular, Examples 1-2 illustrate the synthesis of TRIP compounds in accordance with embodiments of the invention; Example 3 describes experiments illustrating the effects of the compounds in accordance with embodiments of the invention; Example 4 illustrates the effects of different chemical substitutions on TRIP-mediated T cell activation as measured by IFN-γ/IL-2 expression; Example 5 describes a study illustrating the necessity of monitoring the immune status of patients when designing a treatment regimen that combines antigen-specific immunotherapy with chemoradiotherapy; and Example 6 describes a study in which an immunomodulator is used to improve the antitumor effects of, and the immune response to, a peptide cancer vaccine.

Example 1: Synthesis of Z-2-[4-(4-chloro-1,2-diphenyl-but-1-enyl)-phenoxy]ethanol (ospemifene)

Z-1-[4-(2-benzyloxyethoxy)-phenyl]-4-chloro-1,2-diphenyl-but-1-ene (36 g, 0.08 mol) is dissolved in a mixture of ethyl acetate (350 ml) and ethanol (350 ml). Then add palladium on carbon (5%, 0.28 g) and flush the solution with hydrogen gas until no starting material remains. Reaction progress is monitored using thin layer chromatography. Once the reaction is complete, the palladium on carbon is then filtered off through siliceous earth, followed by evaporation of the filtrate. The residue is then crystallized from a mixture of ethanol (155 ml) and water (65 ml). The crystals formed are ospemifene.

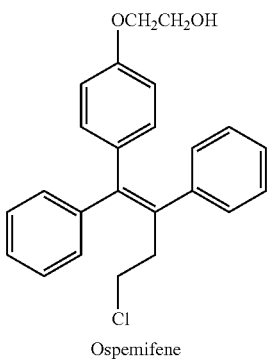

Ospemifene

Example 2: Synthesis of Z-2-{2-[4-(4-chloro-1,2-diphenyl-but-1-enyl)-phenoxy]-ethoxy}-ethanol (fispemifene)

{2-[4-(4-Chloro-1,2-diphenyl-but-1-enyl)-phenoxy]-ethoxy}-acetic acid ethyl ester is dissolved in tetrahydrofuran at room temperature under a nitrogen atmosphere. Then add lithium aluminum hydride to the solution in small portions until the reduction reaction is complete. Reaction progress is monitored by thin layer chromatography. The completed reaction is quenched with a saturated aqueous ammonium chloride solution. The product is then extracted into toluene, which is then dried and evaporated under vacuum. The residue is purified with flash chromatography using toluene/triethylamine (9.5:0.5) as the eluent. The purified compound is fispemifene. Fispemifene is an example of a prodrug. In this instance, fispemifene is principally metabolized into ospemifene.

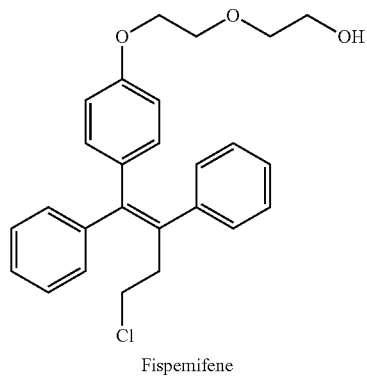 [SMILES: OCCOCCOc1ccc(/C(=C(/CCCl)c2ccccc2)c2ccccc2)cc1]

Fispemifene

Example 3: Triphenylethylene (TRIP) Compounds as Immunomodulators of Vaccine Immune Response Targeted for Cancer and Infectious Diseases Six experiments were conducted demonstrating that TRIPs are effective immunomodulators of vaccine immune response targeted for cancer and infectious disease.

Experiment 1. Effects of TRIP on the Expression of IFN-γ and IL-2 In Vitro

The potential immune regulating effects of TRIP and the possible mechanism(s) involved were determined with in vitro experiments examining the expression of T cell activating cytokines in human acute T cell leukemia Jurkat cells. The expression of IFN-γ and IL-2 RNA following exposure to increasing concentrations of TRIP (i.e., ospemifene) were first examined, followed by the effects of combining tamoxifen with TRIP on the expression of these cytokines. Different inhibitors of key T cell activation pathways—trifluoperazine (TFP), an inhibitor of calmodulin, LY294002, an inhibitor of PI3K, and PD98059, a MAPK inhibitor—in combination with TRIP were assessed for their effects on TRIP-induced expression of IFN-γ and IL-2 in Jurkat cells.

FIG. 1 shows the expression of IFN-γ and IL-2 in human Jurkat cells following exposure to TRIP in vitro. Jurkat cells ($2.0 \times 10^6$) were treated with different concentrations of TRIP as indicated on the x-axis for 24 hours. (A) IFN-γ and (B) IL-2 mRNA expression levels were detected by quantitative real-time polymerase chain reaction (qRT-PCR) and normalized with the expression of GAPDH. $*p<0.05$, $p<0.01$, $*p<0.001$. TRIP significantly induced both IFN-γ and IL-2 RNA compared to control in a dose-dependent fashion after 24 hours treatment, suggesting that TRIP has potential immunomodulatory effects by stimulating the expression of key T cell activating cytokines.

Figure 2:
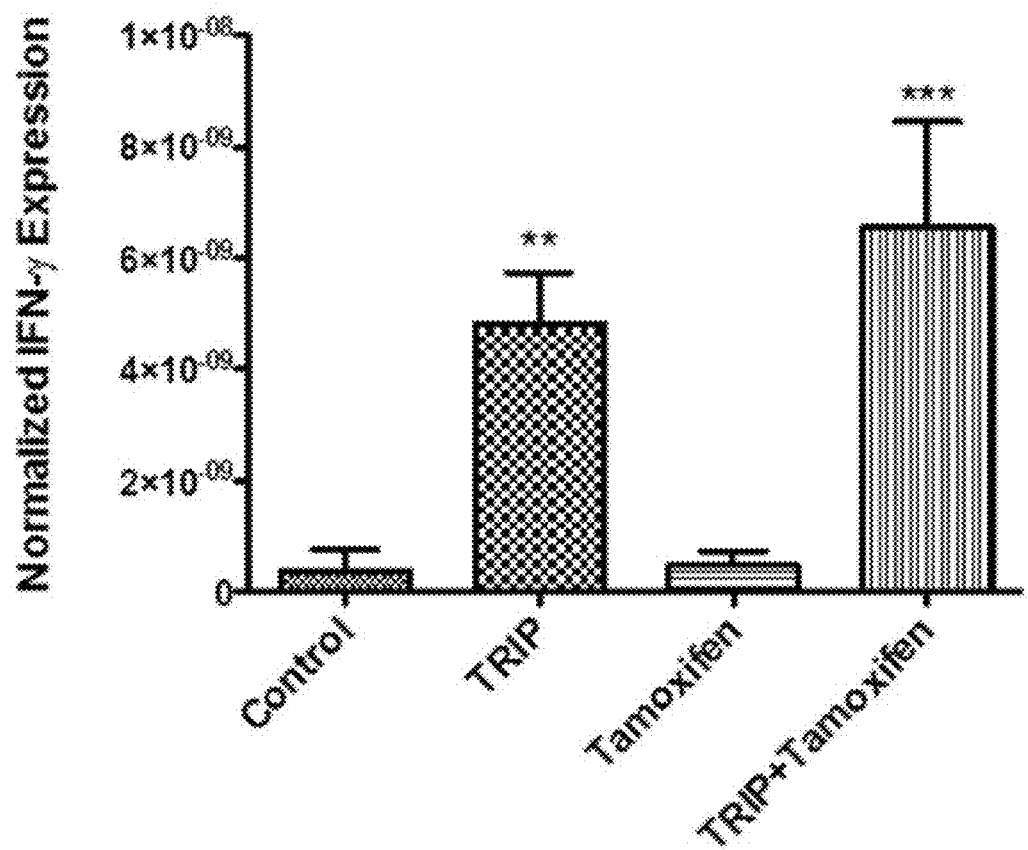
FIG. 2. Effect of tamoxifen on TRIP-induced expression of IFN-γ in vitro. Jurkat cells ($2 \times 10^6$) were treated with TRIP (2.5 μM) and/or tamoxifen (2.5 μM) for 24 hours. The expression levels of IFN-γ were analyzed by qRT-PCR and normalized with GAPDH. $p<0.01$, *$p<0.005$.

FIG. 2 shows the expression of IFN-γ in Jurkat cells following exposure to tamoxifen and TRIP alone and in combination. Tamoxifen has been shown to induce a $T_H2$ immune response, and to determine whether tamoxifen is able to interfere with the immune modulating effect of TRIP, Jurkat cells ($2.0 \times 10^6$) were treated with TRIP (2.5 μM) and/or tamoxifen (2.5 μM) for 24 hours. The expression levels of IFN-γ were analyzed by qRT-PCR and normalized with GAPDH. $p<0.01$, $*p<0.001$. TRIP alone and TRIP+tamoxifen treatments both induced significantly increased expression of IFN-γ compared to control, while tamoxifen had no apparent effect, demonstrating that tamoxifen does not affect the T cell activating ability of TRIP.

Figure 3:
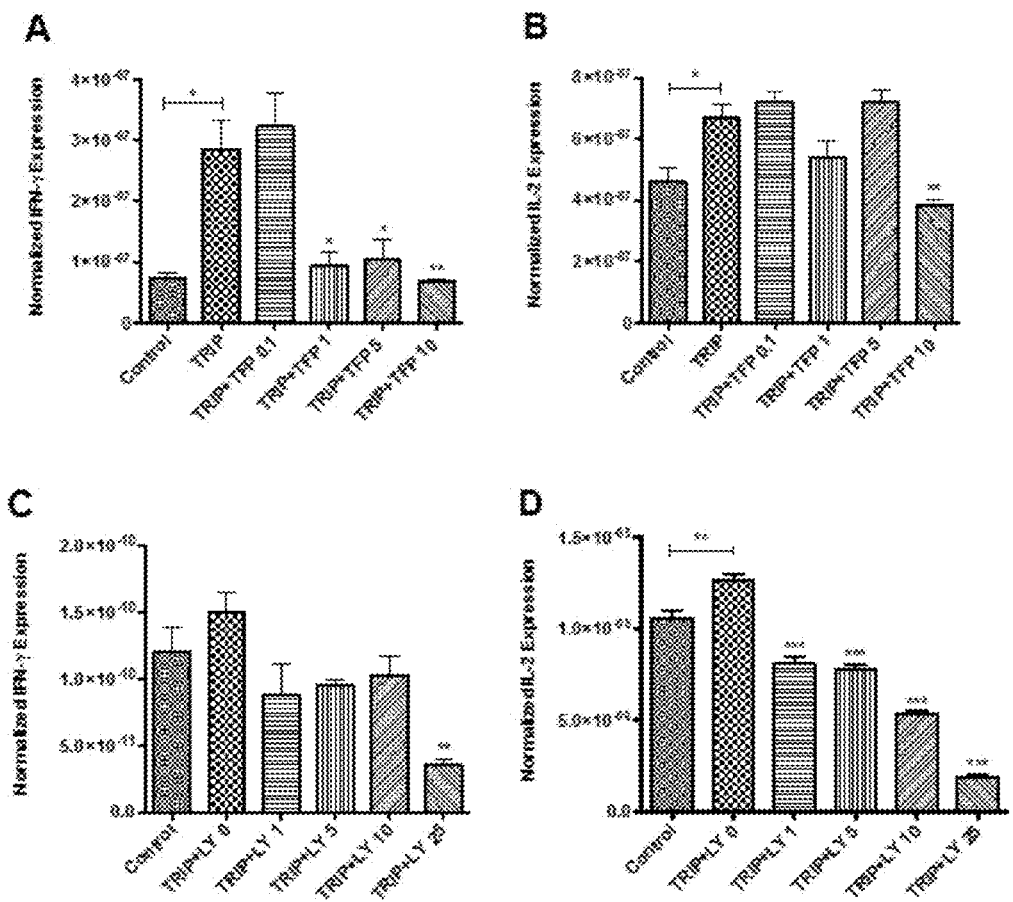
FIG. 3. Effects of TRIP alone and in combination with trifluoperazine (TFP) or LY294002 (LY) on IFN-γ and IL-2 in human Jurkat cells in vitro. Jurkat cells ($2 \times 10^6$) were pretreated with different concentrations of (A, B) TFP (0, 0.1, 1.0, 5.0, and 10.0 μM) and (C, D) LY294002 (0, 1, 5, 10, and 25 μM) for 1 hour, then incubated with medium containing 2.5 μM of TRIP for 24 hours. (A, C) IFN-γ and (B, D) IL-2 mRNA expression levels were detected by qRT-PCR and normalized with the expression of GAPDH. *$p<0.05$, $p<0.01$, *$p<0.001$.

FIG. 3 shows the effects of TRIP alone and in combination with trifluoperazine (TFP) or LY294002 on IFN-γ and IL-2 expression in human Jurkat cells. T cell activation requires multiple signals including PI3K, MAPK and calcium signaling pathways, and in order to identify the potential mechanism through which TRIP affects immune activation, Jurkat cells ($2.0 \times 10^6$) were pretreated with different concentrations of TFP (0, 0.1, 1.0, 5.0 and 10.0 μM) (A, B) or LY294002 (0, 1, 5, 10 and 25 μM) (C, D) for one hour, then incubated with medium containing 2.5 μM TRIP for 24 hours. IFN-γ and IL-2 expression levels were detected by qRT-PCR and normalized with the expression of GAPDH. $*p<0.05$, $p<0.01$, $*p<0.001$. TFP and LY294002 significantly decreased TRIP-induced expression of IFN-γ and IL-2, suggesting that TRIP stimulates T cells through PI3K and calmodulin signaling pathways, which in turn activate the transcription factors NFATc and NF-κB, for both IFN-γ and IL-2.

Figure 4:
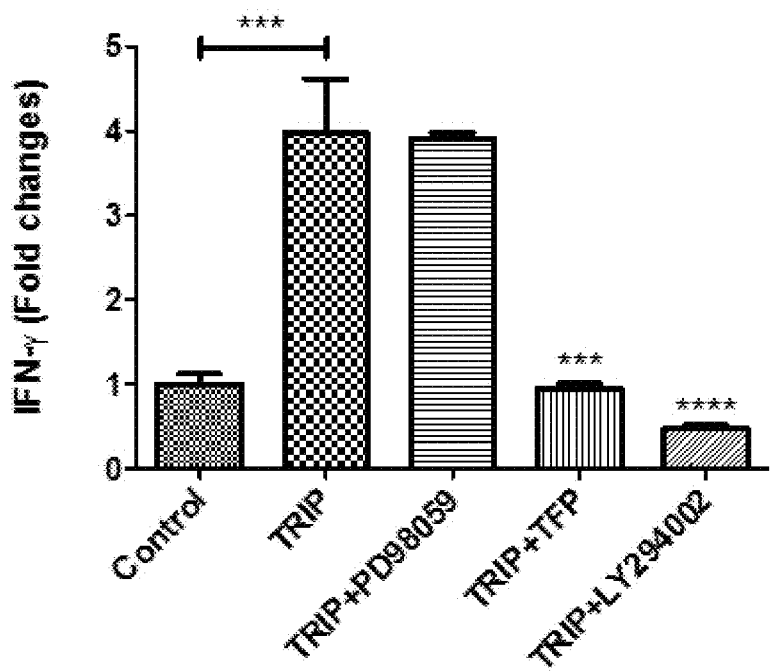
FIG. 4. Effects of calmodulin, PI3K and MAPK inhibition on TRIP-induced expression of IFN-γ and IL-2 in human Jurkat cells in vitro. Jurkat cells ($2 \times 10^6$) were pretreated with PD98059 (50 μM), TFP (10 μM) and LY294002 (25 μM) for 1 hour, then incubated with medium containing 2.5 μM of TRIP for 24 hours. (A) IFN-γ and (B) IL-2 mRNA expression levels were detected by qRT-PCR and normalized with the expression of GAPDH. $p<0.01$, *$p<0.001$, ****$p<0.0001$.
Figure 4:
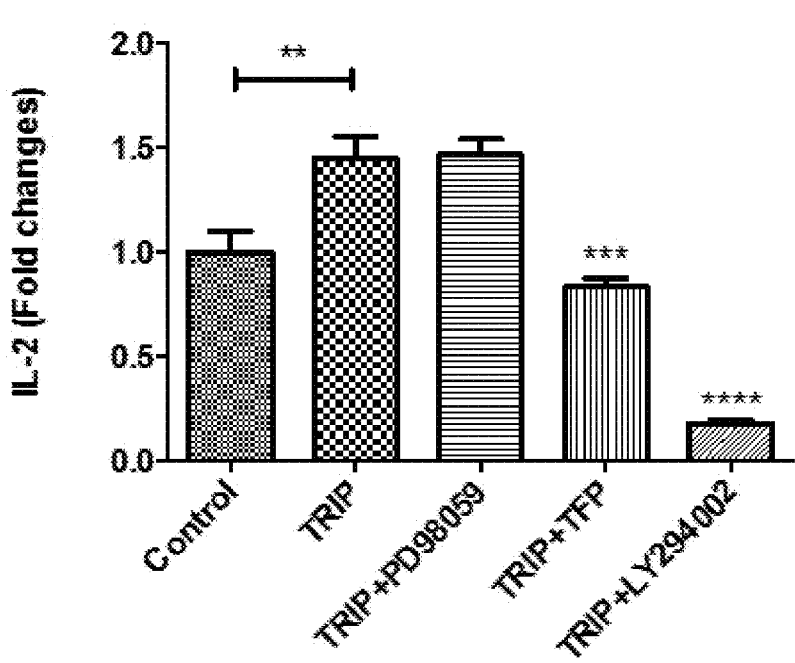

FIG. 4 shows the effects of TRIP alone and in combination with trifluoperazine (TFP), LY294002 or PD98059 on the fold change in expression of IFN-γ and IL-2 in Jurkat cells in vitro. Jurkat cells ($2 \times 10^6$) were pretreated with PD98059 (50 μM), TFP (10 μM) or LY294002 (25 μM) for one hour, then incubated with medium containing 2.5 μM TRIP for 24 hours. (A) IFN-γ and (B) IL-2 mRNA expression levels were detected by qRT-PCR and normalized with expression of GAPDH. $p<0.01$, $*p<0.001$, $****p<0.0001$. As previously demonstrated (see FIG. 3), TFP and LY294002 significantly decreased the TRIP-induced expression of both IFN-γ and IL-2, while PD98059 did not appear to affect the TRIP-induced expression of either cytokine, suggesting that the MAPK kinase pathway does not play a major role in the immune activation effects of TRIP.

Overall, experiment 1 showed that TRIP significantly induced both IFN-γ and IL-2 RNA, suggesting immunomodulatory effects of TRIP. The results further showed that TRIP activates T cells through PI3K and calmodulin signaling pathways and tamoxifen had no discernable effect on TRIP-induced IFN-γ expression.

Experiment 2. Enhancing Antigen-Specific Immunotherapy with TRIPs.

Experiment 2 was designed to test if TRIPs can enhance the immune response to antigen-specific peptide cancer vaccine immunotherapy.

A total of 43 wild type C57BL/6 mice were assigned to four different treatment groups: Control (n=10); and TRIP (i.e., ospemifene) 10, 50, and 100 mg/kg (n=11, all TRIP groups). All mice received a full course of tecemotide (L-BLP25) peptide vaccine (PV) immunotherapy (eight weekly 10 μg doses administered subcutaneously (s.c.) as described in Wurz G T. et al., *J. Transl. Med.*, 11:64 (2013)). During the final 16 days of immunotherapy, mice received daily oral doses of TRIP according to treatment group assignment. TRIP oral dosing solutions were prepared by dissolving an appropriate amount of the drug in pure dimethyl sulfoxide (DMSO) and then adding peanut oil to the desired final concentration (final DMSO concentration was 2%). All doses were administered in a volume of 100 μl using 20-gauge stainless steel oral feeding needles. Control mice were given diluent only. Forty-eight hours following the final dose of PV, all mice were euthanized for the collection of blood for cytokine analysis by multiplex and spleens for assessing immune response by enzyme-linked immunosorbent spot (ELISpot) assay.

Figure 5:
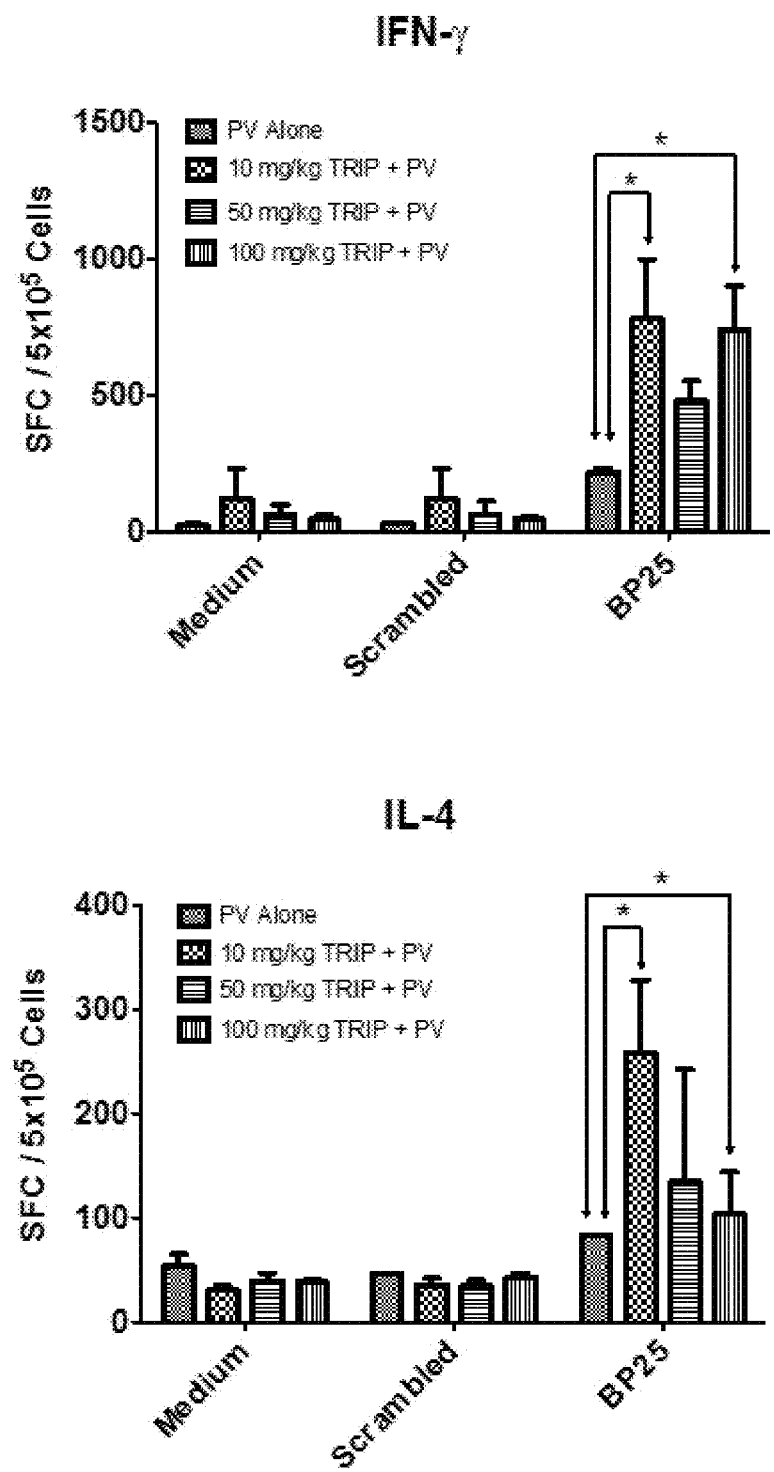
FIG. 5. Effect of TRIP on the immune response to an antigen-specific peptide vaccine (PV). Mice received 8 weekly 10-μg doses of PV and daily oral TRIP treatment for the final 16 days of the study. Lymphocytes were isolated 48 hours after the final dose of PV for the enzyme-linked immunosorbent spot (ELISpot) assay. Data are expressed as the number of spot forming cells (SFC)/500,000 lymphocytes following exposure to medium (no peptide), scrambled peptide, and BP25 peptide. PV=peptide vaccine; *$p<0.05$.

FIG. 5 shows the IFN-γ and interleukin (IL)-4 immune responses, as assessed by ELISpot, to PV immunotherapy in control mice (PV alone) compared to mice treated with a combination of PV and TRIP at 10, 50, and 100 mg/kg. Data are expressed as the number of spot forming cells (SFC)/ 500,000 lymphocytes following exposure to medium (no peptide), scrambled peptide, and BP25 peptide. PV=tecemotide (L-BLP25) peptide vaccine; $*p<0.05$. For IFN-γ, the main T-helper 1 ($T_H1$) cytokine, TRIP appeared to significantly increase the immune response when combined with PV. For IL-4, the main $T_H2$ cytokine, the immune response appeared to decrease with TRIP dose. No significant difference in IL-4 response was observed between mice treated with PV alone and those treated with the combination of PV and 50 mg/kg TRIP.

Serum cytokine analysis revealed that TRIP increased IFN-γ levels (FIG. 6, top) and dose-dependently decreased concentrations of the major inflammatory cytokine IL-6 (FIG. 6, bottom) in non-tumor bearing mice treated with the combination of TRIP and PV compared to mice treated with PV alone. This shows that TRIPs enhance a specific immune response in a dose-dependent manner.

Figure 6:
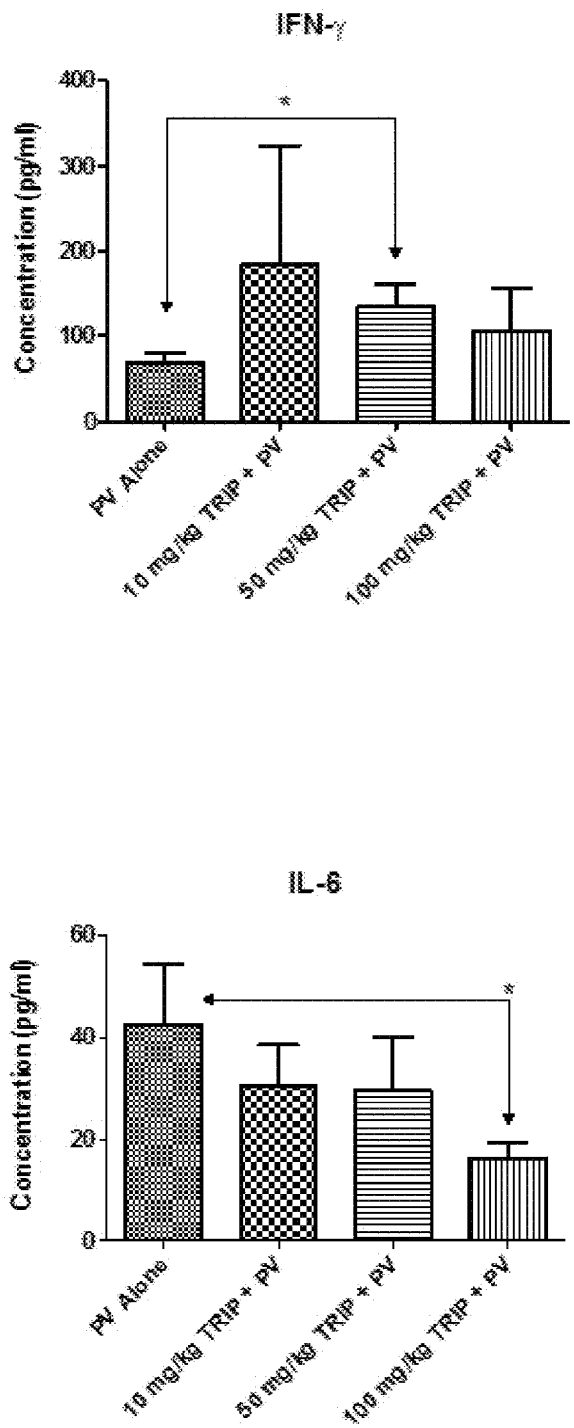
FIG. 6. Effect of TRIP and PV combination treatment on serum cytokine levels. Serum cytokines were assessed by multiplex immunoassay 48 hours following the final dose of PV, which was administered as 8 weekly 10-μg doses. TRIP was administered daily for the last 14 days of the study. PV=peptide vaccine; *$p<0.05$.

As shown in FIG. 6, significant differences in IFN-γ were observed between mice treated with the combination of TRIP 50 mg/kg and PV compared to PV alone. Serum concentrations of IL-6 were significantly lower in mice treated with the combination of TRIP 100 mg/kg and PV compared to PV alone. This demonstrates that a biphasic action can be achieved with TRIPs; that is, an enhanced antigen-specific immune response while reducing serum IL-6 cytokine levels associated with inflammation.

Overall, experiment 2 demonstrates that short-course treatment with both low (10 mg/kg) and high (100 mg/kg) doses of TRIP significantly increased the antigen-specific immune response to the PV. Enhancement of a vaccine's immune response with TRIPs offers improved treatments for certain types of cancer as well as infectious diseases.

Experiment 3. Biphasic Action of TRIPs on Immune Response and Inflammation.

Experiment 3 was designed to test if TRIPs can reduce inflammatory cytokines associated with lung tumor progression in a dose-dependent manner. This activity can be useful in enhancing the effectiveness of therapeutic agents used in treating cancer including chemoradiotherapy.

Following induction of lung cancer as described (Wurz G T. et al., *J. Transl. Med.*, 11:64 (2013)), mice were randomized into four treatment groups: Control; and TRIP (i.e., ospemifene) 5, 25, and 50 mg/kg (n=12, all groups). TRIP and control solutions were orally administered by gavage according to treatment group. After 30 days of treatment (Week 20), a total of 16 mice, four from each treatment group, were euthanized, and whole blood was collected by cardiac puncture. The remaining mice continued daily TRIP treatments. An additional 16 mice, four from each treatment group, were euthanized following 60 (Week 24) and 90 (Week 28) days of treatment, and whole blood and livers were collected. Serum samples were subjected to multiplex cytokine analysis for $T_H1$ (IL-2, IL-12, IFN-γ, TNF-α), $T_H2$ (IL-4, IL-5, IL-10, IL-13) and inflammatory cytokines (MIP-1α, IP-10, MIG, IL-1β, IL-6, KC).

Figure 7:
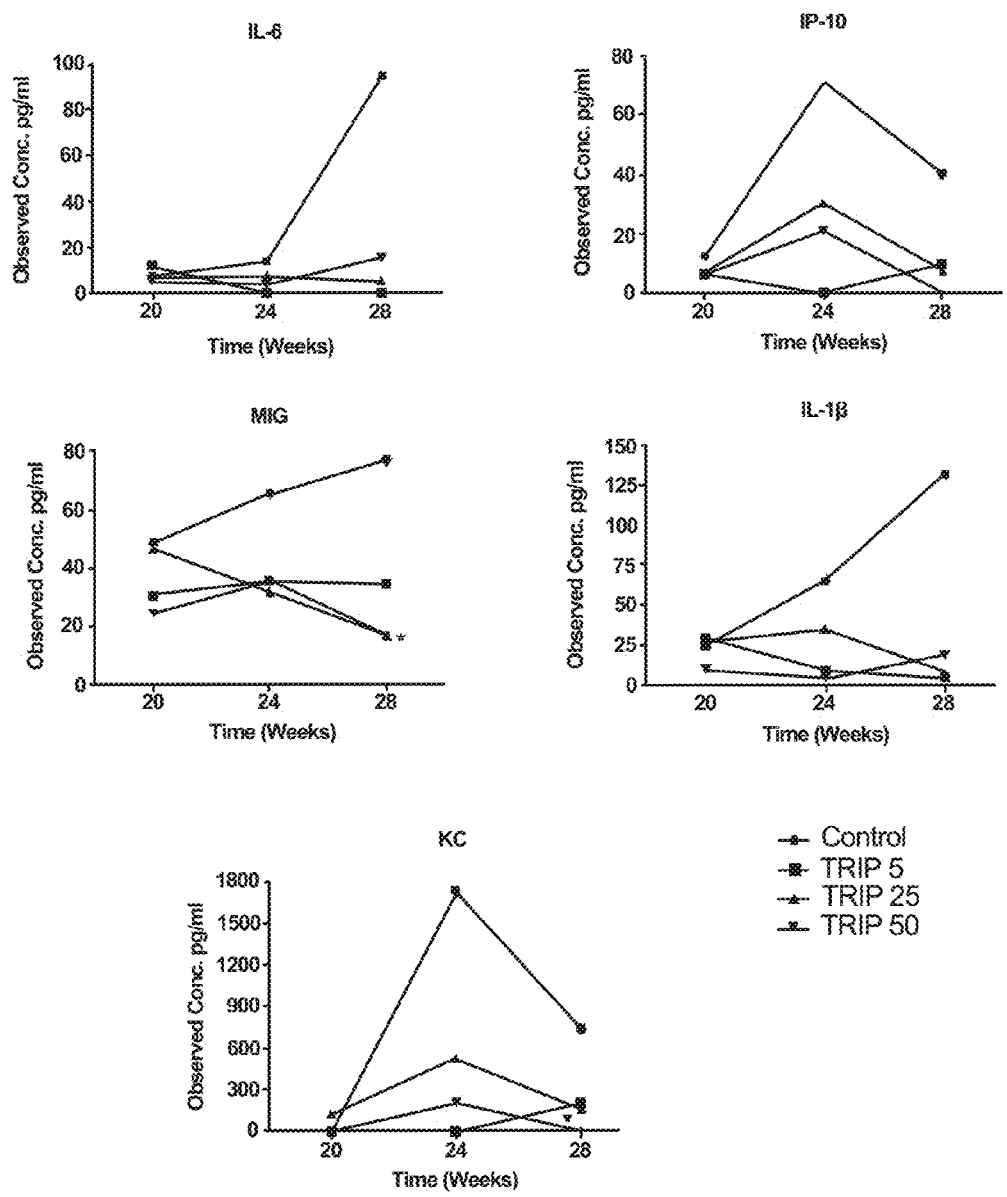
FIG. 7. Average serum pro-inflammatory cytokine concentrations after 30 (Week 20), 60 (Week 24), and 90 (Week 28) days of daily oral TRIP treatment at the indicated doses (mg/kg). Serum was analyzed by multiplex immunoassay 24 hours following the last dose of TRIP at each time point.

Terminal serum pro-inflammatory cytokines (IL-6, IP-10, MIG, IL-1β, KC) were analyzed 24 hours after the last dose at each time point (FIG. 7). As determined by multiplex analysis, noticeable differences were found in pro-inflammatory serum cytokine levels of the control group compared to the treated groups. Increasing pro-inflammatory serum cytokine levels in the control mice may be a result of an inflammatory response associated with tumor progression. In contrast, the decreasing levels of pro-inflammatory serum cytokines in the TRIP-treated mice may suggest an anti-inflammatory effect. Differences in IL-6 levels were observed at 28 weeks between control and all doses of TRIP.

Figure 8:
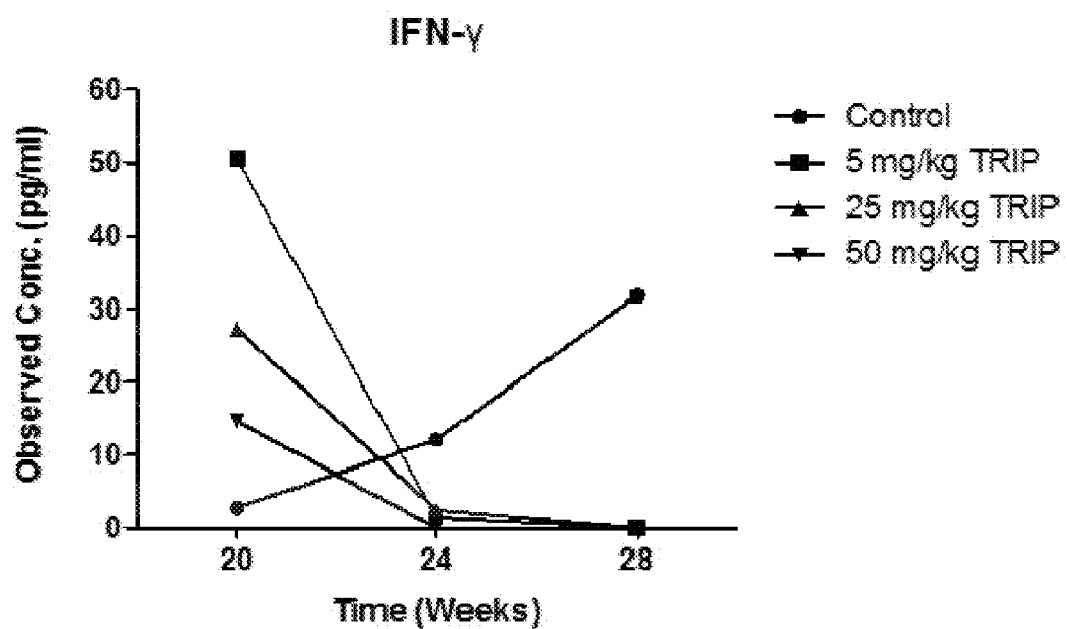
FIG. 8. Average serum IFN-γ concentrations following daily oral TRIP treatment for 30 (Week 20), 60 (Week 24), and 90 (Week 28) days at the indicated doses (mg/kg). Serum was analyzed by multiplex immunoassay 24 hours after the final TRIP dose at each time point.

A major $T_H1$ cytokine, IFN-γ, was elevated at 20 weeks at the 5-mg/kg TRIP dose level (FIG. 8). The synthetic estrogen diethylstilbestrol has been shown to have effects similar to estradiol on T-lymphocyte cytokine production (Karpuzoglu-Sahin E. et al., *J. Reprod. Immunol.*, 52:113-27 (2001)), while the potent antiestrogen acolbifene has been shown to antagonize this effect (Suzuki T. et al., *Am. J. Physiol. Cell Physiol.*, 292:C2103-11 (2007)).

Overall, the third experiment illustrates the dose-dependent effect on serum cytokines associated with a $T_H1$ response and inflammation. The results of this study have multiple applications in enhancing immunotherapies while decreasing tumor inflammation, which in turn may enhance the efficacy of therapeutic agents used in treating cancer including chemoradiotherapy. For example, pretreatment with TRIPs enhance a cancer vaccine's immune response followed by a reduction of serum cytokines associated with tumor inflammation, which in turn may optimize the antitumor response to chemoradiotherapy.

Abbreviations: TNF-α (tumor necrosis factor alpha); MIP-1α (macrophage inflammatory protein-1 alpha); IP-10 (interferon gamma-induced protein 10); MIG (interferon gamma-induced protein 10); KC (keratinocyte derived cytokine).

Experiment 4. Enhancing Antigen-Specific Immunotherapy with TRIPs Following Short-Course Treatment in Lung Tumor-Bearing Mice The goal of experiment 4 was to evaluate the effect of short-course TRIP treatment on the immune response to an antigen-specific cancer immunotherapy in tumor-bearing mice.

A total of 65 male human MUC1.Tg C57BL/6 mice underwent urethane lung tumor induction as described (Wurz G T. et al., *J. Transl. Med.*, 11:64 (2013)) starting at approximately five weeks of age. In Week 20, six weeks after the last dose of urethane, mice were randomized into six treatment groups of approximately equal average weight: Control (n=10); TRIP (i.e., ospemifene) 10 mg/kg (n=11); TRIP 50 mg/kg (n=11); tecemotide (L-BLP25) peptide vaccine (PV) alone (n=11); TRIP 10 mg/kg+PV (n=11); and TRIP 50 mg/kg+PV (n=11). Starting in Week 20, all mice in the PV treatment groups were administered eight weekly 10 μg doses by subcutaneous (s.c.) injection (100 μl) at rotating sites using a 25-gauge needle. For the last 16 days of the study, mice assigned to TRIP treatment were administered daily oral doses prepared as described above under Experiment 2. All other mice received daily oral doses of the control solution. Twenty-four hours after the final dose of TRIP and 48 hours after the last dose of PV (Week 27), all mice were euthanized for the collection of serum and spleens, which were processed appropriately for ELISpot and CTL assays. For the ELISpot assay, n=4-5.

Figure 9:
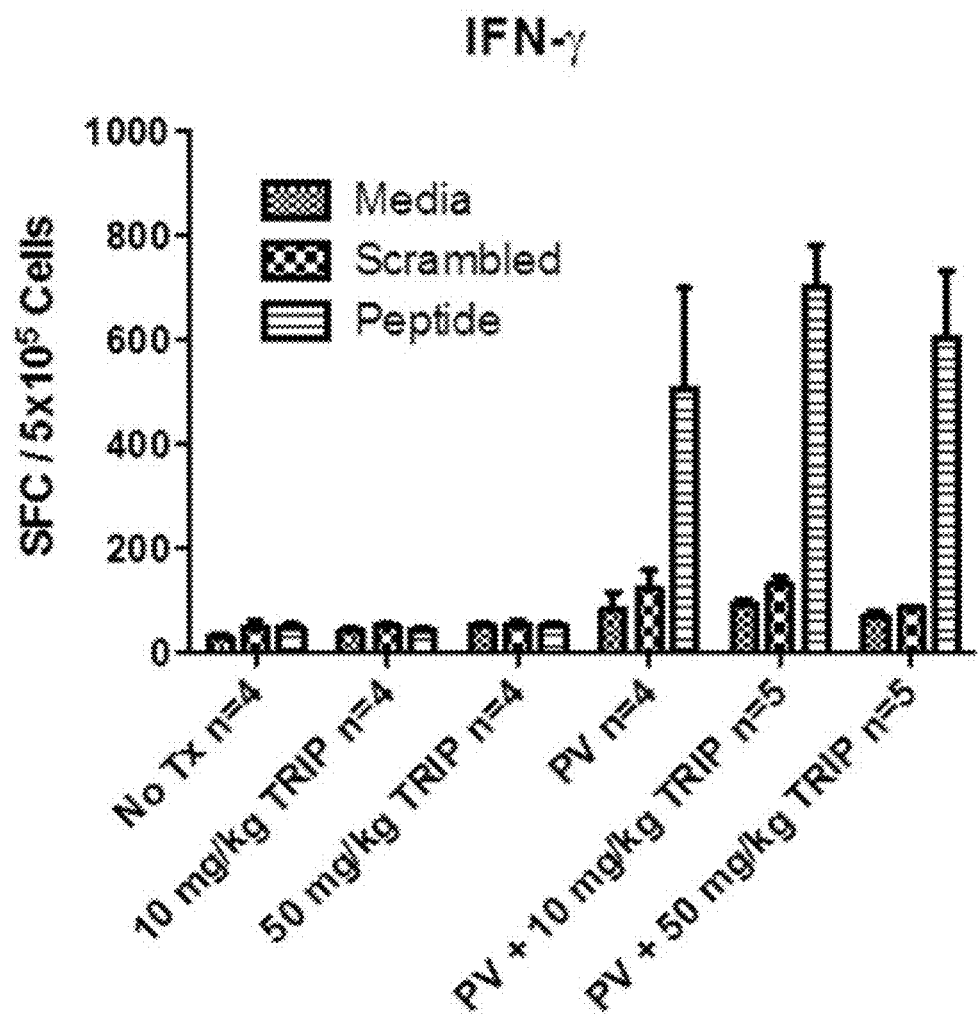
FIG. 9. Effect of short-course (16-day) TRIP treatment on IFN-γ immune response. Average (+SEM) spot forming cells (SFC) from an ELISpot assay (n=4-5) following exposure of lymphocytes to no peptide (media), scrambled peptide (scrambled), and active peptide (peptide) are shown. Lymphocytes were isolated following treatment with one cycle of PV, TRIP 10 mg/kg, TRIP 50 mg/kg, or combinations (n=10-11). PV=peptide vaccine.
Figure 10:
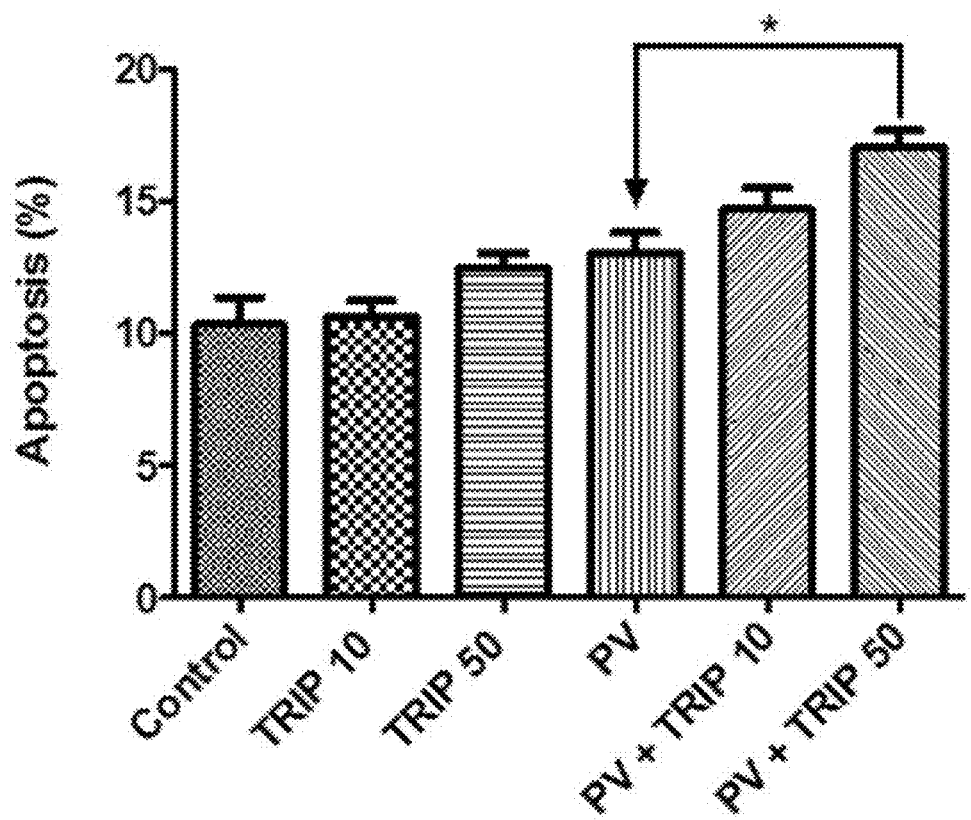
FIG. 10. Effects of short-course TRIP dosing regimens on cytotoxic T lymphocyte activity. Average target cell apoptosis percentages (+SEM) were assessed in control (n=10), one cycle of PV (n=11), short-course TRIP (16 days; 10 mg/kg, TRIP 10; 50 mg/kg, TRIP 50; n=11), and PV+TRIP combination (n=11) treatment groups. PV=peptide vaccine; $*p<0.05$.

As shown in FIG. 9, although the IFN-γ immune response showed an equivalent increase with both TRIP in combination with the PV and PV alone, the combination of PV with short-course TRIP (50 mg/kg) significantly boosted the induction of CTL activity compared to TRIP or PV treatments alone (FIG. 10). Indeed, FIG. 10 illustrates the effects of short-course TRIP dosing regimens on cytotoxic T lymphocyte apoptosis activity. Average target cell apoptosis percentages (+SEM) were assessed in control (n=10), one cycle of PV (n=11), short-course TRIP (16 days; 10 mg/kg, TRIP 10; 50 mg/kg, TRIP 50; n=11), and PV+TRIP combination (n=11) treatment groups. PV=peptide vaccine; *p<0.05.

The fourth experiment illustrates that high-dose (50 mg/kg), short-course TRIP treatment in combination with PV significantly increased cytotoxic T lymphocyte (CTL) activity compared to PV alone.

Experiment 5. Effects of Short-Course, High-Dose TRIP Compared to Estradiol and Letrozole on Immune Status The goal of experiment 5 was to evaluate the antiestrogenic effects on immune status of high-dose TRIP compared to both estradiol and letrozole.

A total of 32 female human MUC1.Tg C57BL/6 mice, starting at approximately six weeks of age, were treated with urethane as described (Wurz G T. et al., *J. Transl. Med.*, 11:64 (2013)). Two weeks following the final dose of urethane (Week 17), the mice were randomized into four treatment groups of approximately equal average weight (n=8, all groups): Control (no treatment); TRIP (i.e., ospemifene) 100 mg/kg; estradiol 25 μg/kg; and letrozole 0.8 mg/kg. TRIP and letrozole were prepared in DMSO and peanut oil as described above in Experiment 2 and administered daily for 14 days by oral gavage (100 μL). Estradiol was dissolved in 100% ethanol, diluted in PBS to achieve the desired concentration, and then administered daily for 14 days by s.c. injection at rotating sites using a 25-gauge needle. In Week 19, the study was terminated, 24 hours after the last treatments, and serum and spleens were collected for surface marker and Treg analyses.

Figure 11:
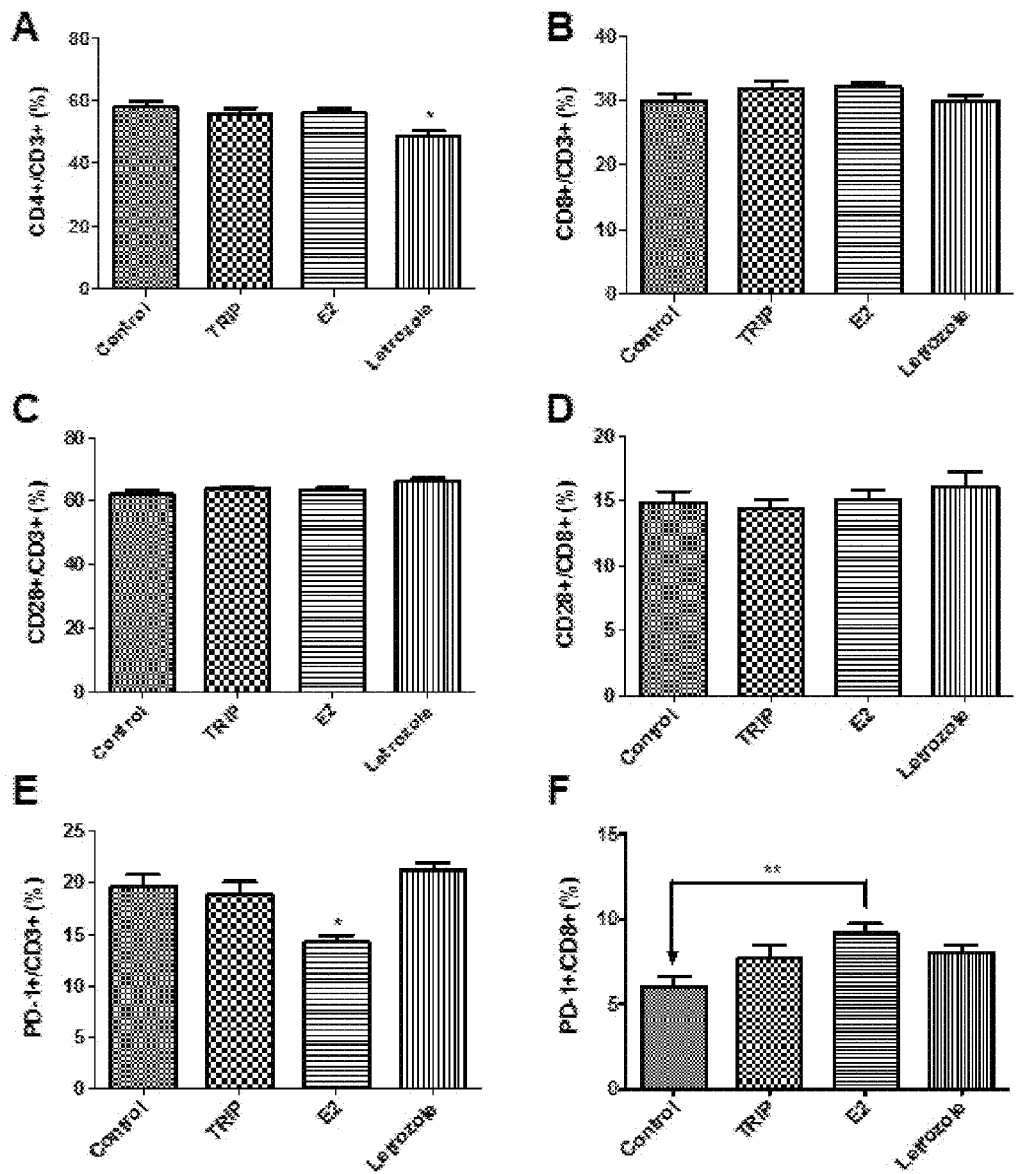
FIG. 11. Lymphocyte phenotypes following different hormonal treatments. (A) CD3+CD4+; (B) CD3+CD8+; (C) CD3+CD28+; (D) CD8+CD28+; (E) CD3+PD-1+; and (F) CD8+PD-1+; T cell surface markers were stained with indicated antibodies after 15 days of TRIP (100 mg/kg), estradiol (E2; 25 μg/kg), and letrozole (0.8 mg/kg) treatments (n=8 all groups). Proportions (+SEM) of cells positive for the indicated markers are shown. $*p<0.05$, $**p<0.01$.
Figure 12:
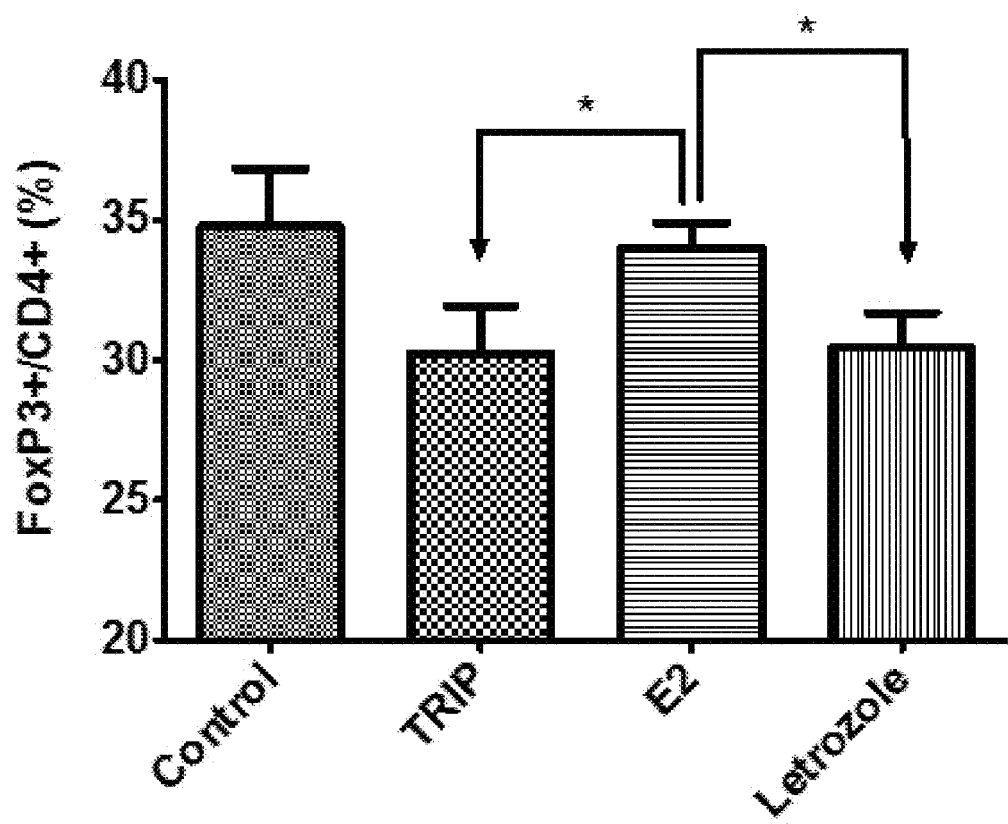
FIG. 12. Short-course, high-dose TRIP and letrozole reduce regulatory T cell (Treg) expression. Average proportions (+SEM) of CD4+FoxP3+ cells (Tregs) among total CD4+ cells from untreated control, TRIP (100 mg/kg), estradiol (E2; 25 μg/kg), and letrozole (0.8 mg/kg) groups were analyzed following daily treatment for 15 days (n=8 all groups). $*p<0.05$.
Figure 13:
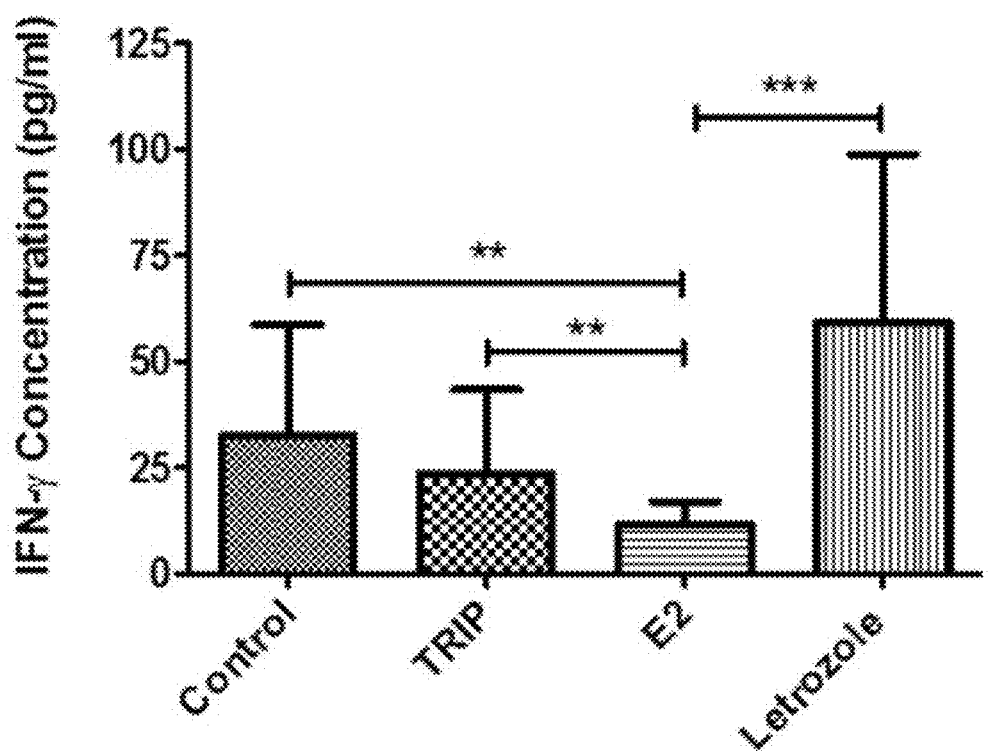
FIG. 13. Effects of TRIP on serum IFN-γ compared to estradiol and letrozole. Serum IFN-γ from untreated control, TRIP (100 mg/kg), estradiol (E2; 25 μg/kg), and letrozole (0.8 mg/kg) groups were analyzed following daily treatment for 14 days (n=8 all groups). $p<0.01$, $*p<0.001$.

After two weeks of treatment, lymphocytes were isolated from spleen. T-cell surface markers (CD4, CD8, PD-1, CD28) and regulatory T cells (Tregs) were analyzed by flow cytometry. As shown in FIG. 11, there was no difference in the expression of surface markers, including CD8 (FIG. 11B) and CD28 (FIGS. 11C and 11D), among TRIP, letrozole and control groups, except that the CD4+ T cell population was lower in the letrozole-treated group (FIG. 11A). However, the total PD-1+ T lymphocyte population was significantly decreased in the estradiol-treated group (FIG. 11E) compared to control. Further analysis of the subpopulation of PD-1+ T lymphocytes showed that the percentage of PD-1+/CD8+ T cells was significantly increased upon estradiol treatment compared to control (FIG. 11F). In order to determine whether TRIP was inducing an immunosuppressive tumor microenviroment, similar to tamoxifen, the percentage of T-regs (FoxP3+/CD4+) in all treatment groups was analyzed (FIG. 12). The data showed that both TRIP and letrozole treatments significantly inhibited Tregs compared to estradiol treatment. These results are consistent with observations from the serum IFN-γ cytokine analysis (FIG. 13) showing that high doses of TRIP act differently from estradiol.

Overall, the fifth experiment illustrates that while no meaningful differences in T-cell surface marker expression among the treatment groups was measured, estradiol treatment significantly increased the percentage of PD-1+/CD8+ T cells compared to control. Both TRIP and letrozole treatments significantly inhibited Tregs compared to estradiol treatment. Serum IFN-γ analysis showed that both TRIP and letrozole significantly increased concentrations compared to estradiol. The results of Experiments 4 and 5 further support the biphasic effects of TRIPs on immune response.

Experiment 6. Effects of Chronic TRIP Dosing on Immune Response

The goal of this experiment 6 was to evaluate the effects of TRIP on immune status and immune response to peptide vaccine immunotherapy following chronic dosing in tumor-bearing mice.

A total of 55 mixed-sex hMUC1.Tg C57BL/6 mice, starting at approximately five weeks of age, were treated with urethane as described above. Approximately six weeks after the last dose of urethane, mice were randomized into four treatment groups of approximately equal average weight: Control (n=22); TRIP (i.e., ospemifene) 50 mg/kg (n=16); tecemotide (L-BLP25) peptide vaccine (PV) (n=6); and TRIP+PV (n=11). At this time (Week 21), mice assigned to the TRIP groups began treatment with the first of two cycles consisting of eight weekly 10 µg doses each, with approximately four weeks between cycles. Cycle 1 was administered during Weeks 21-28, and Cycle 2 from Weeks 32-39. The PV was prepared and administered as described above. Mice in the TRIP groups began daily oral treatment in Week 31, which continued through the end of the study (approximately eight weeks of dosing). TRIP was prepared and administered as described above. Mice not assigned to TRIP treatment received daily oral doses of diluent. At the conclusion of the study, 48 h after the final dose of PV and 24 h after the last dose of TRIP, all mice were euthanized for the collection of serum and spleens, which were processed as described above for multiplex serum cytokine, Treg, and CTL analyses.

Figure 14:
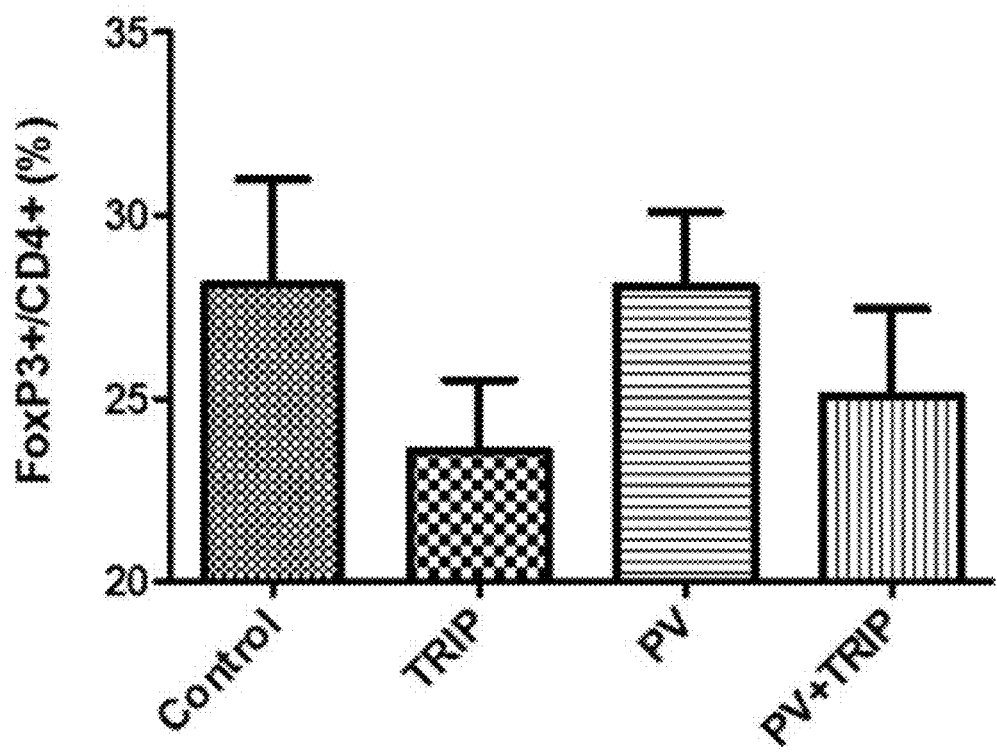
FIG. 14. Effects of TRIP on regulatory T cell (Treg) expression following chronic dosing. Average Treg expression (+SEM) following nine weeks of chronic daily TRIP dosing (50 mg/kg; n=16) compared to control (n=22), peptide vaccine (PV) (n=6), and TRIP+PV (n=11).
Figure 15:
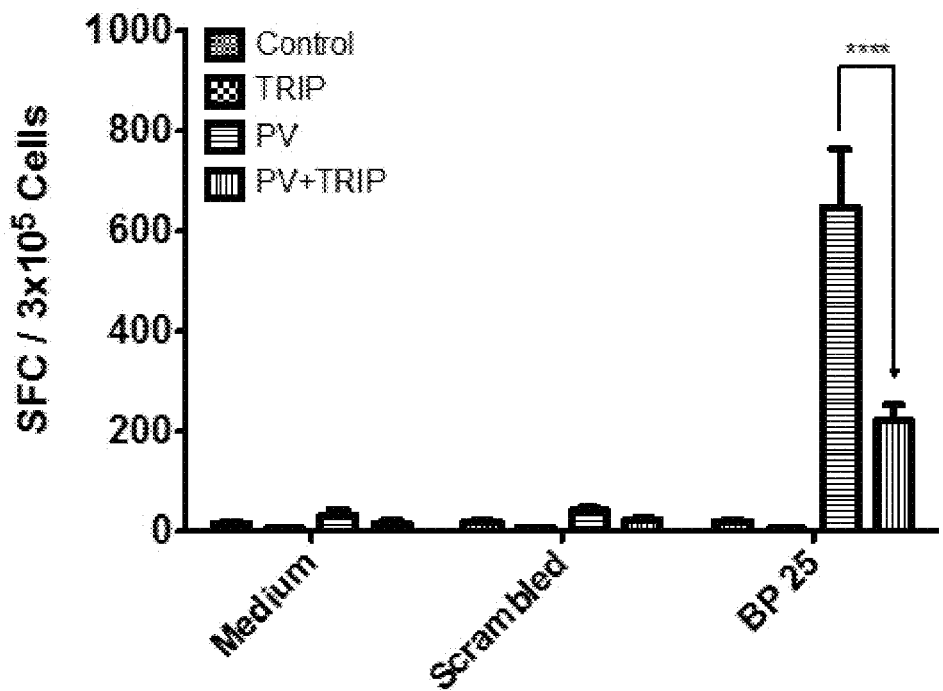
FIG. 15. Effects of TRIP on IFN-γ immune response and cytotoxic T lymphocyte activity following chronic dosing. Antigen-specific IFN-γ immune response was assessed by ELISpot 48 hours following two cycles of peptide vaccine (PV). (A) Average spot forming cells (SFC/3×10$^5$ cells+SEM) of TRIP dosing (50 mg/kg; n=16) compared to control (n=22), PV (n=6), and TRIP+PV (n=11) following nine weeks of chronic daily dosing. (B) Average target cell apoptosis percentages (+SEM) were assessed in the same treatment groups as described above. $*p<0.05$, $****p<0.0001$.
Figure 15:
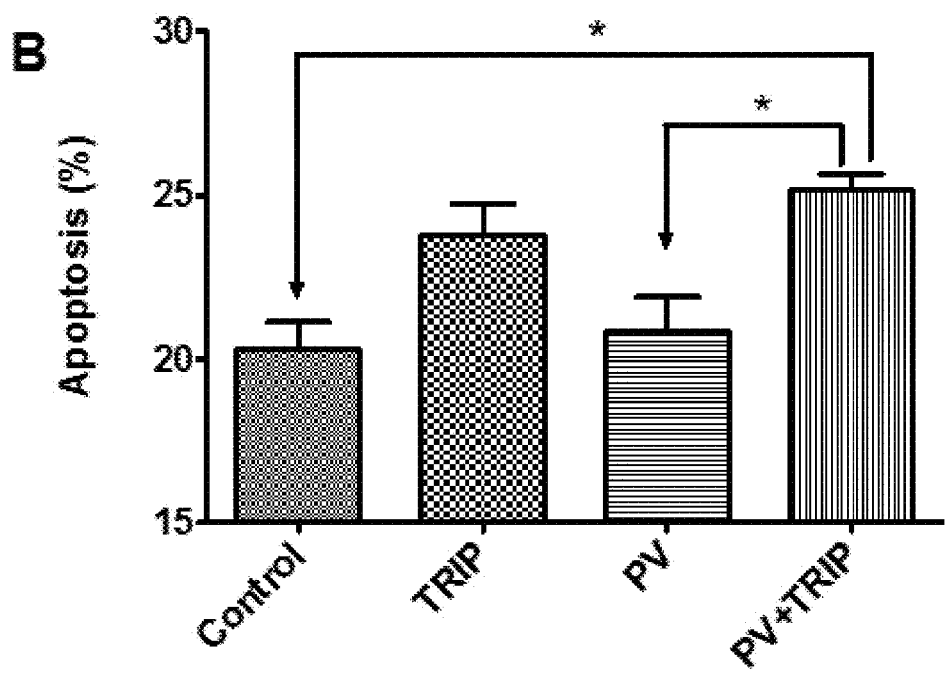

As shown in FIG. 14, as assessed by Treg expression, chronic dosing with TRIP did not significantly affect the PV-induced immune response. This is in contrast to the effects of short-course treatment with TRIP (see FIG. 10). The PV-induced, antigen-specific immune response was significantly decreased following chronic TRIP dosing (FIG. 15A). With respect to CTL activity (FIG. 15B), chronic dose TRIP induced slightly, but not significantly increased activity compared to control. However, no additive CTL activity was observed in combination with PV. Although it appears that chronic TRIP dosing did not improve the PV immune response as shown in FIG. 15A, the combination increased CTL activity over that of PV alone (FIG. 15B).

Overall, the sixth experiment illustrates that, as assessed by Treg expression, chronic TRIP dosing did not affect PV-induced immune response, in contrast to the effects of short-course treatment. The specific immune response to PV was significantly decreased by chronic TRIP dosing, which also resulted in a slightly, but not significantly increased CTL response. Unlike short-course treatment, no additive CTL activity was observed in combination with PV following chronic dosing with TRIP.

Example 4: Effects of Different Chemical Substitutions on TRIP-Mediated T Cell Activation as Measured by IFN-γ/IL-2 Expression The effects on T cell activation of different functional group substitutions on the TRIP chemical structure (Formula Ia) were examined by measuring the expression of IFN-γ and IL-2 RNA in human acute T cell leukemia Jurkat cells in vitro. The results of these experiments are shown in Table 1.

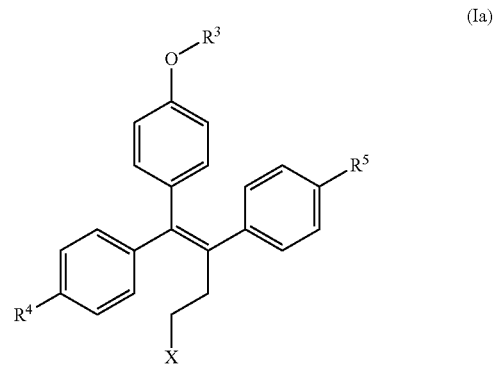

(Ia)

TABLE 1

Relative effects of different chemical substitutions on T cell activation as measured by IFN-γ/IL-2 mRNA expression.

| R Substitution | IFN-γ Expression[1] | IL-2 Expression[1] |
| --- | --- | --- |
| $R_3 = CH_2CH_2OH$; $R_4 = H$; $R_5 = H$, X = Cl | +++ | +++ |
| $R_3 = CH_2CH_2OH$; $R_4 = OH$; $R_5 = H$, X = Cl | +++ | +++ |
| $R_3 = CH_2CH_2OCH_2CH_2OH$; $R_4 = H$; $R_5 = H$, X = Cl | +++ | +++ |
| $R_3 = H$; $R_4 = H$; $R_5 = H$, X = Cl | + | − |
| $R_3 = CH_2COOCH_3$; $R_4 = OH$; $R_5 = H$, X = Cl | − | − |
| $R_3 = CH_2COOH$; $R_4 = H$; $R_5 = H$, X = Cl | − | − |
| $R_3 = CH_2CH_2NHCH_3$; $R_4 = OH$; $R_5 = H$, X = Cl | − | − |
| $R_3 = CH_2CH_2NH_2$; $R_4 = H$; $R_5 = H$, X = Cl | − | − |

[1]+++ (strong increase); ++ (moderate increase); + (weak increase); − (no effect).

The relative effects of expression are based on the level of expression in a control sample that did not receive a TRIP compound. A strong increase is defined as a ≥50% increase compared to the control. A moderate increase is defined as a 25-49% increase compared to the control. A weak increase is defined as a 0-24% increase compared to the control. No effect is when there was no increase compared to the control.

This example demonstrates that changes in the TRIP chemical structure, particularly the $R_3$ side chain, have a major impact on T cell activation (structure activity relationships—SARs) as measured by IFN-γ/IL-2 RNA expression, and thus the effectiveness of different TRIP compounds as immunomodulators. The presence of functional groups such as tertiary amines or carboxylic acids in the $R_3$ side chain resulted in a lack of T cell activation.

Figure 16:
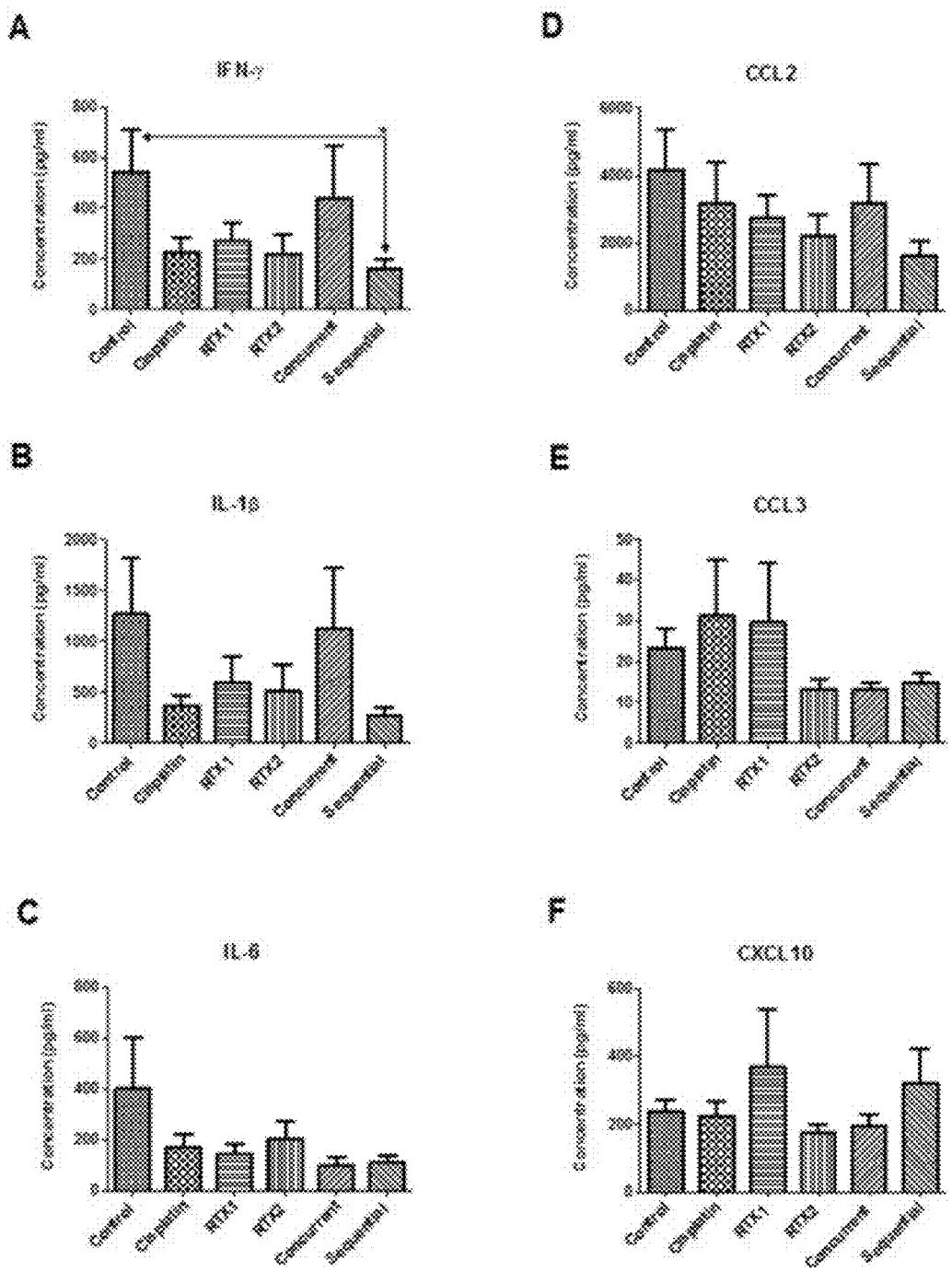
FIG. 16. Effects of cisplatin chemotherapy, radiotherapy, and concurrent and sequential cisplatin/radiotherapy on proinflammatory serum cytokines—IFN-γ (A), IL-1β (B), IL-6 (C)—and chemokines—CCL2 (D), CCL3 (E), CXCL10 (F)—(mean+SEM). For all treatment groups in each panel, n=19-23. A statistically significant difference (p=0.03) was observed in serum IFN-γ in mice treated with sequential cisplatin/radiotherapy compared to control.
Figure 17:
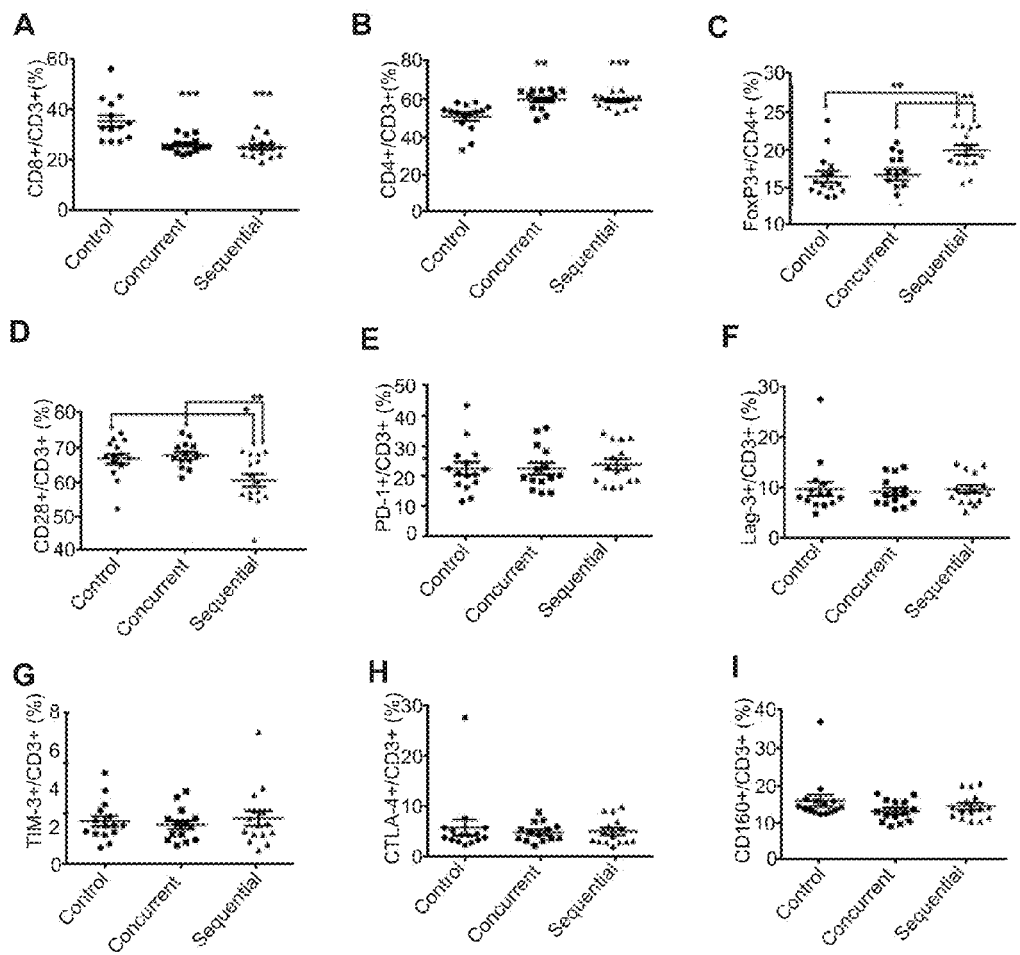
FIG. 17. Effects of concurrent and sequential cisplatin/radiotherapy on lymphocyte surface markers. CD8 (A), CD4 (B), CD4+FoxP3+"Treg" (C), CD28 (D), PD-1 (E), Lag-3 (F), TIM-3 (G), CTLA-4 (H), CD160 (I) are shown. Values represent the percentage of the total CD3 population (CD4 population for panel C) positive for each respective marker (mean±SEM). For all panels, n=14-15 for control, concurrent and sequential. In panels A and B, $p<0.01$ vs. control, $*p<0.001$ vs. control; in panels C and D, $*p<0.05$ and $**p<0.01$ for the indicated comparisons.

Example 5: Assessing the Effects of Concurrent vs. Sequential Cisplatin/Radiotherapy on Immune Status in C57BL/6 Mice Both concurrent and sequential cisplatin-based chemoradiotherapy (CRT) are standard therapeutic approaches in cancer treatment. Recent clinical data suggest that these different dosing schedules may adversely affect antigen-specific immunotherapy. To determine the effect of concurrent and sequential cisplatin/radiotherapy on the immune system, we assessed the levels of six different cytokines, which include proinflammatory cytokines (IFN-γ, IL-1β, and IL-6) and chemokines (CCL2, CCL3, and CXCL10) in serum to monitor changes in the immune response following chemotherapy and/or radiotherapy (FIG. 16). Although no significant differences among the treated groups were observed, the level of IFN-γ was significantly lower following sequential cisplatin/radiotherapy compared to the control mice (p=0.03) (FIG. 16A). Next, we examined the lymphocyte populations by surface marker staining. As shown in FIGS. 17A and 17B, cytotoxic CD8+ T cells were significantly downregulated, whereas CD4+ T cells were upregulated in both concurrent and sequential cisplatin/radiotherapy compared to control. It is well known that CD4+ T cells including helper, memory, and regulatory T cells are important for immune regulation. Among the CD4+ subsets, CD4+FoxP3+ regulatory T cells (Treg), also known as suppressor T cells, are crucial for tumor immune escape by suppressing antitumor immune responses. The increase of CD4+ T cells after cisplatin/radiotherapy prompted us to ask whether Treg cells were also modulated. Interestingly, only sequential cisplatin/radiotherapy treatment induced significant upregulation of Treg cells compared to control and concurrent treatment groups (FIG. 17C). We further examined the expression of other inhibitory markers such as PD-1, CTLA-4, Lag3, TIM3, and CD160, but no significant difference was observed in any of these markers compared to control (FIGS. 17E-I). However, CD28, a co-stimulatory molecule that is essential for T cell activation, was significantly decreased following sequential cisplatin/radiotherapy compared to control and concurrent treatment groups, while concurrent cisplatin/radiotherapy did not affect CD28 expression (FIG. 17D). This result indicates that sequential cisplatin/radiotherapy induced an immune suppressive environment that may result in immune tolerance for cancer or may interfere with the response to immunotherapy (Kao C J. et al., *Cancer Immunol. Res.*, 3:741-50 (2015)).

This study demonstrates that there are key differences in immune status following either concurrent or sequential CRT, and indicates that immune status should be monitored throughout treatment with CRT when combined with immunotherapy. The continuous monitoring of the individual patient's immune system before, during, and after therapy may guide the ideal timing of immunotherapy on an individual patient basis (DeGregorio M. et al., *OncoImmunology*, 1:1422-4 (2012)), and when a TRIP immunomodulator should be employed.

Example 6: Using an Immunomodulator to Boost the Antitumor Effects of Immunotherapy and Increase the Immune Response Example 5 illustrated the necessity of monitoring the immune status of patients when designing treatment regimens that combine antigen-specific immunotherapy with CRT. Example 6 tests the effects of using an immunomodulator in combination with a peptide cancer vaccine and if the combination therapy can increase the antitumor effects and boost the T cell immune response to antigen-specific immunotherapy.

A total of 32 female C57BL/6 wild type mice were assigned to four treatment groups (n=8): Control; TRIP (i.e., ospemifene) 100 mg/kg; tecemotide (L-BLP25) peptide vaccine (PV) (100 µg); and TRIP 100 mg/kg combined with 100 µg PV. On Day 0 of the study, all 32 mice were subcutaneously implanted with $1.0 \times 10^6$ mouse breast cancer cells expressing the PV target antigen (BP25). Two days later, mice began a three-day regimen of once daily 100 mg/kg TRIP administered orally. On Day 5, mice were administered their first weekly 100 µg dose of PV by subcutaneous injection. This treatment schedule was repeated for a total of four weeks. Tumor growth was assessed twice weekly. All mice were euthanized on Day 28 for the collection of serum and spleens to assess immune response to treatment. Immune response was assessed by performing IFN-γ ELISpot.

Figure 18:
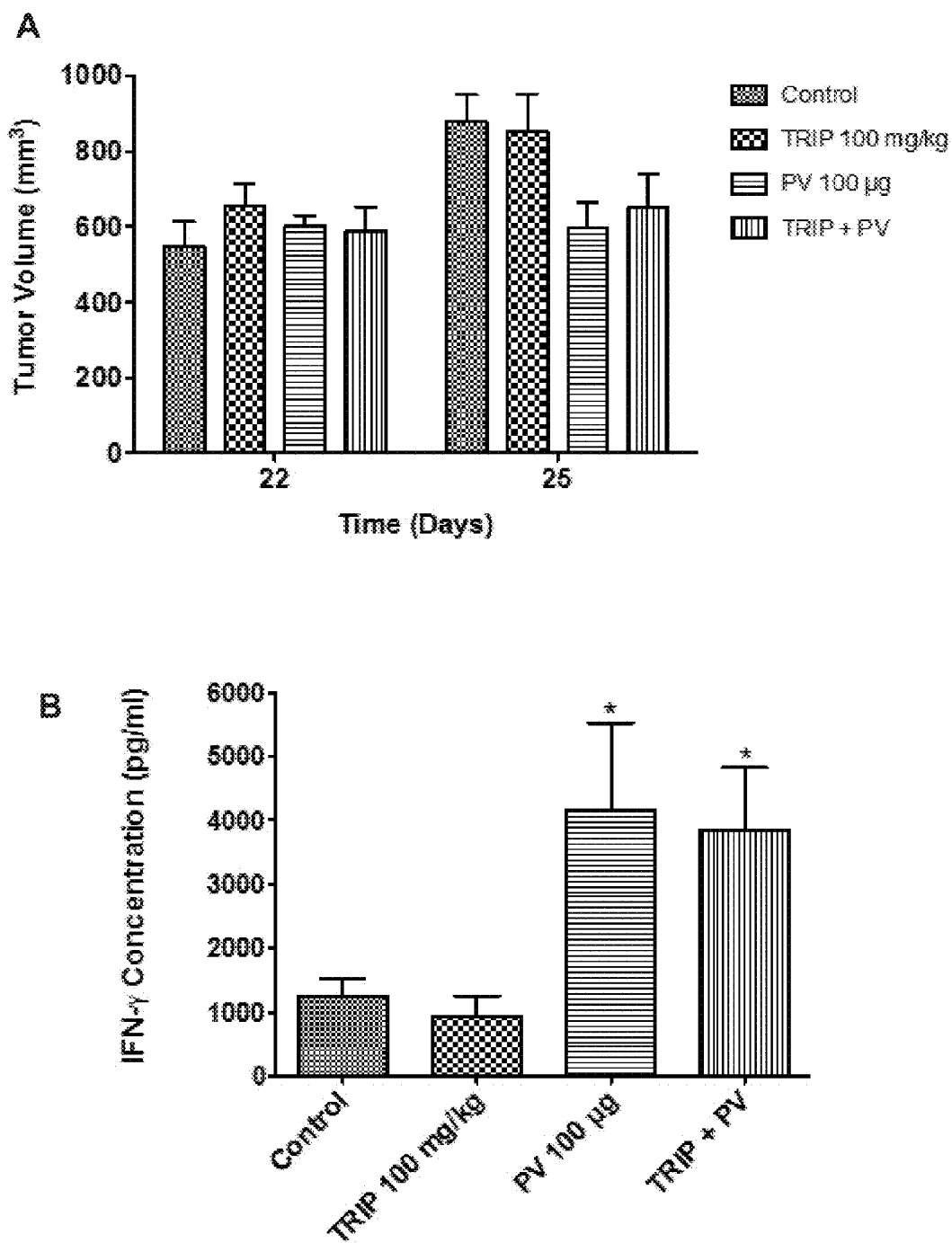
FIG. 18. Antitumor effects and serum IFN-γ immune response to peptide vaccine immunotherapy alone and in combination with TRIP immunomodulator. Each of four weekly 100-μg injections of peptide vaccine (PV) was preceded by three daily oral doses of TRIP (100 mg/kg). All mice were implanted with breast cancer allografts on Day 0, and serum was collected on Day 28 following four weeks of treatment. Tumor volumes were measured twice each week. For all treatment groups, n=8. (A) Average tumor volumes (+SEM) are shown for Days 22 and 25 along with (B) serum IFN-γ levels as assessed on Day 28. $*p<0.05$ compared to both control and TRIP 100 mg/kg.

As shown in FIG. 18A, treatment with PV alone and in combination with TRIP reduced tumor volume compared to the control group as measured on Days 22 and 25. The serum IFN-γ immune response on Day 28, 48 hours following the fourth and final dose of PV is shown in FIG. 18B. Both vaccinated groups demonstrated significantly increased levels of serum IFN-γ compared to the control and TRIP alone treatment groups. As shown in FIG. 19, when the T cell immune response was assessed by ELISpot, both groups treated with PV showed specific IFN-γ responses to the target antigen (BP25); however, the mice treated with PV in combination with TRIP showed an increased immune response compared to the mice treated with PV alone. Again, short course dosing schedules of TRIPs can enhance an antigen-specific therapy.

This study demonstrates that using an immunomodulator in combination with a peptide cancer vaccine can increase the antitumor effects and boost the T cell immune response to antigen-specific immunotherapy. Thus, the immune status of cancer patients can be assessed prior to and during treatment with immunotherapy, and if necessary, an immunomodulator can be administered to potentially boost a patient's immune response so that they may derive increased benefits from immunotherapy.

Example 7: Using an Immunomodulator to Boost the Effective Immune Response to the Influenza Vaccine in Subjects Above 50 Years of Age The immunosenescence of subjects of above 50 years of age, and especially those above 65, reduces the effective immune response. Standard techniques to improve the immune response of these individuals typically involve administering a high-dose formulation of the vaccine containing four times the amount of antigen compared to the standard formulation. This technique, however, does not amount to a significant improvement in the protection against influenza virus. The following example illustrates a method for improving the effective immune response to the influenza vaccine in subjects above 50 years of age using TRIP compounds in combination with the vaccine.

The influenza vaccine is prepared with a normal amount of antigen and administered via subcutaneous injection. One day prior to administration of the influenza vaccine, patients take an oral dose of an effective amount of an ospemifene tablet. In some cases, an effective amount is about 5 mg/kg of ospemifene where the kg refers to the total weight of the individual receiving treatment. In other cases, the effective amount is about 2 mg/kg or about 10 mg/kg ospemifene.

For patients with known immunodeficiency disorders or severe immunosenescence, more than one oral dose of ospemifene is provided. These patients take daily oral doses of ospemifene for seven days and receive an additional influenza antigen injection on the fourth day after the initial injection to boost the effective immune response.

Effective immune response is measured by measuring the IFN-γ immune response from serum harvested from patients that received the vaccine (or the vaccine and two additional injections of ospemifene) when exposed to cells infected with the influenza virus. A boosted immune response is one that increases the IFN-γ immune response compared to similarly aged individuals that only received the vaccine without ospemifene.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for modulating an immune response to a therapeutic agent in a subject, the method comprising administering an effective amount of a compound according to Formula I

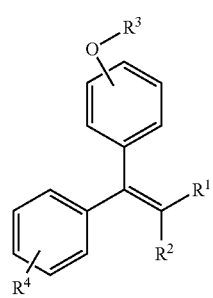

(I)

or a pharmaceutically acceptable salt thereof in combination with an effective amount of the therapeutic agent to the subject, wherein:

$R^1$ and $R^2$ are selected from the group consisting of

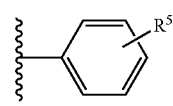

and a $C_{1-8}$ haloalkyl, wherein when $R^1$ is

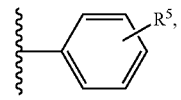

$R^2$ is a $C_{1-8}$ haloalkyl, and when $R^1$ is a $C_{1-8}$ haloalkyl, $R^2$ is

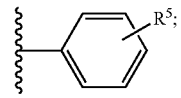

the $C_{1-8}$ haloalkyl comprises a halogen X; and $R^3$, $R^4$, and $R^5$ are independently selected from the group consisting of hydrogen, a hydroxyl, a $C_{1-18}$ alkylhydroxy, and an alkoxy.

2. The method of claim 1, wherein the $C_{1-8}$ haloalkyl is

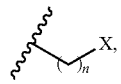

wherein the subscript n is an integer selected from the group consisting of 1, 2, 3, and 4.

3. The method of claim 2, wherein

is

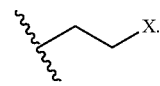

4. The method of claim 1, wherein X is Cl.

5. The method of claim 1, wherein $R^3$, $R^4$, and $R^5$ are independently selected from the group consisting of hydrogen, a hydroxyl, a $C_{2-10}$ alkylhydroxy, and an alkoxy, wherein the alkoxy comprises $C_{2-6}$ and at least one bridging oxygen atom.

6. The method of claim 1, wherein the compound of Formula I is represented by Formula Ia

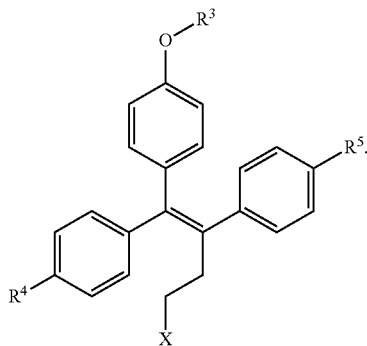

(Ia)

7. The method of claim 1, wherein the compound of Formula I is represented by Formula Ib

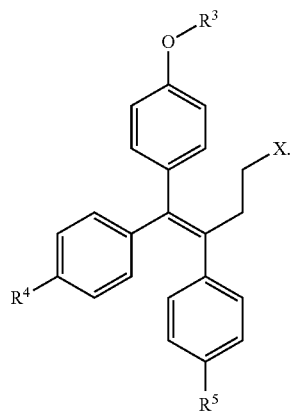

(Ib)

8. The method of claim 6, wherein
$R^3$ is an alkoxy or alkylhydroxyl,
$R^4$ is hydrogen or a hydroxyl,
$R^5$ is hydrogen, and
X is Cl.

9. The method of claim 8, where $R^3$ is

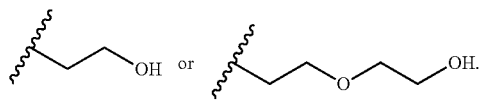

10. The method of claim 1, wherein the subject has or is at risk of developing cancer.

11. The method of claim 10, wherein the therapeutic agent is selected from the group consisting of a chemotherapeutic agent, a radiotherapeutic agent, an antigen-specific immunotherapeutic agent, an endocrine therapy, a tyrosine kinase inhibitor, a thalidomide derivative, and combinations thereof.

12. The method of claim 11, wherein the antigen-specific immunotherapeutic agent is selected from the group consisting of a vaccine, an antibody, cytotoxic T lymphocytes (CTLs), chimeric antigen receptor T cells (CAR-T cells), and combinations thereof.

13. The method of claim 12, wherein the vaccine is a peptide vaccine.

14. The method of claim 1, wherein the subject has or is at risk of developing an infectious disease.

15. The method of claim 14, wherein the infectious disease is caused by a virus, a bacterium, a fungi, or a parasite.

16. The method of claim 15, wherein the virus is a filovirus.

17. The method of claim 14, wherein the therapeutic agent is selected from the group consisting of an antigen-specific immunotherapeutic agent, an antiviral, an antibiotic, and antifungal, a thalidomide derivative, and combinations thereof.

18. The method of claim 17, wherein the antigen-specific immunotherapeutic agent is a vaccine or an antibody.

19. The method of claim 18, wherein the vaccine is a peptide vaccine.

20. The method of claim 1, wherein the compound of Formula I enhances the immune response of the subject to the therapeutic agent.

21. The method of claim 20, wherein the compound of Formula I enhances the immune response by improving the T cell response, augmenting the innate T cell immune response, decreasing inflammation, inhibiting T regulatory cell activity, or combinations thereof.

22. The method of claim 1, wherein the compound of Formula I is administered before the therapeutic agent is administered.

23. The method of claim 1, wherein the effective amount of the compound of Formula I is an amount sufficient to first improve the T cell response and then decrease inflammation.

24. The method of claim 23, wherein different doses of the compound of Formula I are administered to the subject in accordance with a sequential dosing regimen.

25. The method of claim 1, wherein the method comprises:
(a) administering a first dosing regimen of an effective amount of the compound of Formula I in combination with an effective amount of a first therapeutic agent to the subject, wherein the effective amount of the compound of Formula I is an amount sufficient to enhance the T cell response to the first therapeutic agent; and
(b) administering a second dosing regimen of an effective amount of the compound of Formula I in combination with an effective amount of a second therapeutic agent to the subject, wherein the effective amount of the compound of Formula I is an amount sufficient to decrease inflammation and enhance the response to the second therapeutic agent.

26. The method of claim 25, wherein the first therapeutic agent is an antigen-specific immunotherapeutic agent.

27. The method of claim 26, wherein the antigen-specific immunotherapeutic agent is selected from the group consisting of a vaccine, an antibody, cytotoxic T lymphocytes (CTLs), chimeric antigen receptor T cells (CAR-T cells), and combinations thereof.

28. The method of claim 27, wherein the vaccine is a peptide vaccine.

29. The method of claim 25, wherein the second therapeutic agent is selected from the group consisting of a chemotherapeutic agent, a radiotherapeutic agent, an endocrine therapy, a tyrosine kinase inhibitor, an antiviral, an antibiotic, an antifungal, a thalidomide derivative, and combinations thereof.

30. The method of claim 29, wherein the second therapeutic agent is a chemotherapeutic agent.

31. The method of claim 25, wherein the first dosing regimen is administered before the first therapeutic agent is administered.

32. The method of claim 25, wherein the first and second dosing regimens are administered sequentially.

33. The method of claim 25, wherein the first dosing regimen comprises a high dose of the compound of Formula I and the second dosing regimen comprises a low dose of the compound of Formula I.

* * * * *